(12) United States Patent
Fung et al.

(10) Patent No.: US 11,896,835 B2
(45) Date of Patent: Feb. 13, 2024

(54) ELECTRICAL SHIELDING IN IMPLANTABLE MEDICAL DEVICES

(71) Applicant: Cochlear Limited, Macquarie University (AU)

(72) Inventors: Wilson Fung, Winston Hills (AU); Stuart Tyler, Breakfast Point (AU); Jane Rapsey, Berowra (AU)

(73) Assignee: Cochlear Limited, Macquarie University (AU)

( * ) Notice: Subject to any disclaimer, the term of this patent is extended or adjusted under 35 U.S.C. 154(b) by 283 days.

(21) Appl. No.: 16/758,571

(22) PCT Filed: Oct. 18, 2018

(86) PCT No.: PCT/IB2018/058107
§ 371 (c)(1),
(2) Date: Apr. 23, 2020

(87) PCT Pub. No.: WO2019/082032
PCT Pub. Date: May 2, 2019

(65) Prior Publication Data
US 2020/0346022 A1 Nov. 5, 2020

Related U.S. Application Data

(60) Provisional application No. 62/576,759, filed on Oct. 25, 2017.

(51) Int. Cl.
*A61N 1/375* (2006.01)
*A61N 1/36* (2006.01)
*A61N 1/05* (2006.01)

(52) U.S. Cl.
CPC ......... *A61N 1/3754* (2013.01); *A61N 1/0541* (2013.01); *A61N 1/36038* (2017.08)

(58) Field of Classification Search
None
See application file for complete search history.

(56) References Cited

U.S. PATENT DOCUMENTS

| 4,071,032 A | 1/1978 | Schulman |
| 5,833,714 A | 11/1998 | Loeb |

(Continued)

FOREIGN PATENT DOCUMENTS

| CN | 105992611 A | 10/2016 | |
| CN | 106029168 A | 10/2016 | |
| WO | WO-2004105572 A2 * | 12/2004 | ........... A61N 1/3754 |

OTHER PUBLICATIONS

International Search Report and Written Opinion received in related international application No. PCT/IB2018/058107 dated Apr. 2, 2019 (21 pages).

*Primary Examiner* — Erica S Lee
(74) *Attorney, Agent, or Firm* — Edell, Shapiro & Finnan, LLC

(57) ABSTRACT

Presented herein are implantable medical devices that include an insulator extending through a hermetically-sealed biocompatible housing. A plurality of feedthrough pins, which include at least a first feedthrough pin, a second feedthrough pin, and at least one ground feedthrough pin extend through the insulator. An electrically shielding member is disposed at the outer surface of the insulator so as to provide a grounding barrier between the first and second feedthrough pins.

20 Claims, 17 Drawing Sheets

(56) References Cited

U.S. PATENT DOCUMENTS

| | | | |
|---|---|---|---|
| 6,768,629 B1* | 7/2004 | Allen | H01G 4/35 |
| | | | 29/25.42 |
| 7,164,572 B1 | 1/2007 | Burdon | |
| 7,930,032 B2 | 4/2011 | Teske | |
| 9,511,220 B2 | 12/2016 | Marzano | |
| 2007/0179554 A1 | 8/2007 | Iyer et al. | |
| 2007/0265674 A1 | 11/2007 | Olson | |
| 2010/0202096 A1 | 8/2010 | Iyer | |
| 2011/0102967 A1* | 5/2011 | Munns | A61N 1/3754 |
| | | | 361/302 |
| 2012/0006576 A1 | 1/2012 | Barry et al. | |
| 2013/0215553 A1 | 8/2013 | Iyer | |
| 2014/0083762 A1 | 3/2014 | Barry et al. | |
| 2015/0088226 A1* | 3/2015 | Tourrel | A61N 1/3754 |
| | | | 607/57 |
| 2016/0287883 A1 | 10/2016 | Barry et al. | |
| 2016/0367821 A1 | 12/2016 | Frysz et al. | |
| 2017/0087355 A1 | 3/2017 | Stevenson | |
| 2017/0150600 A1* | 5/2017 | Day | H05K 1/0306 |
| 2019/0060649 A1* | 2/2019 | Van den Heuvel | |
| | | | A61N 1/36038 |

* cited by examiner

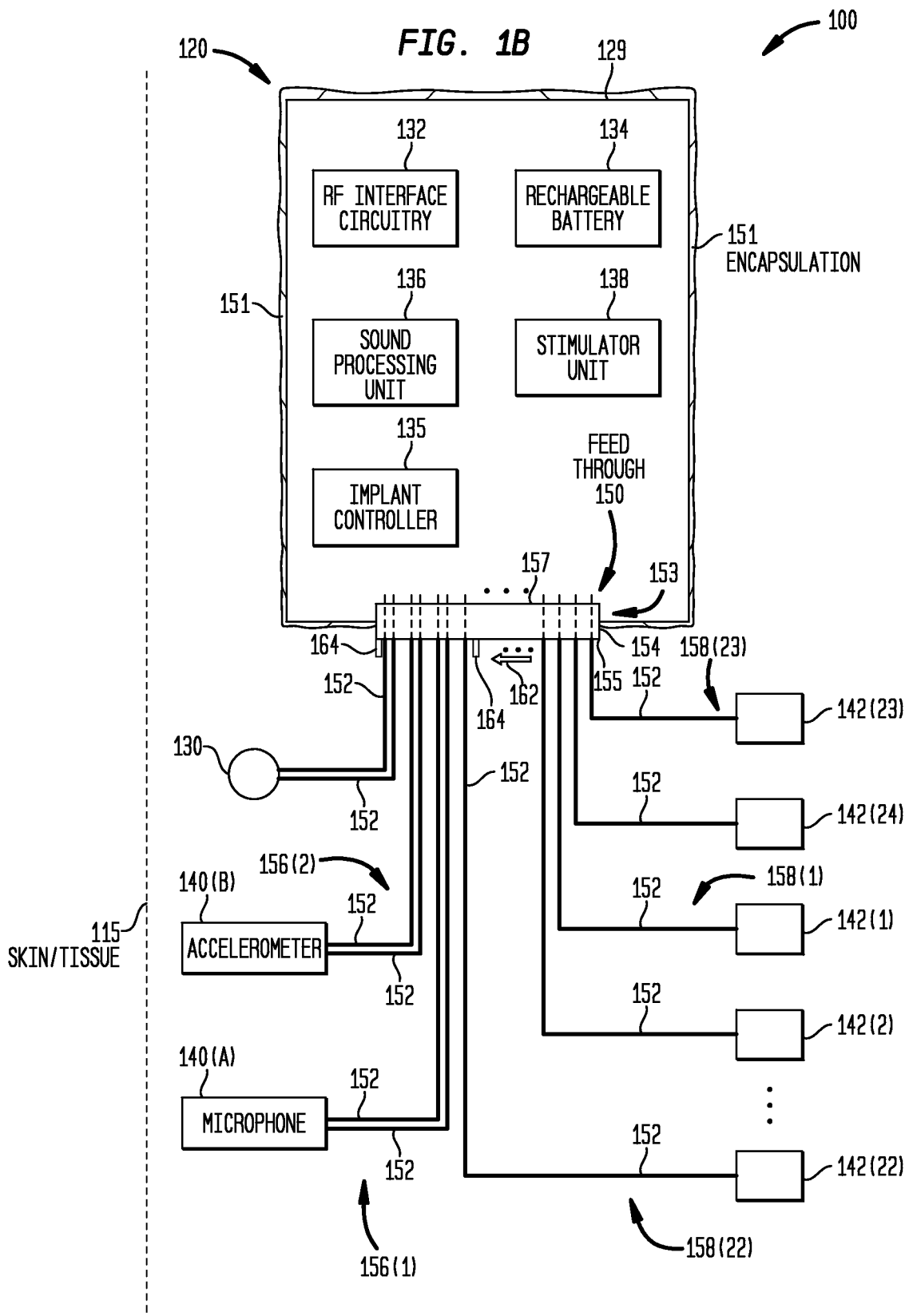

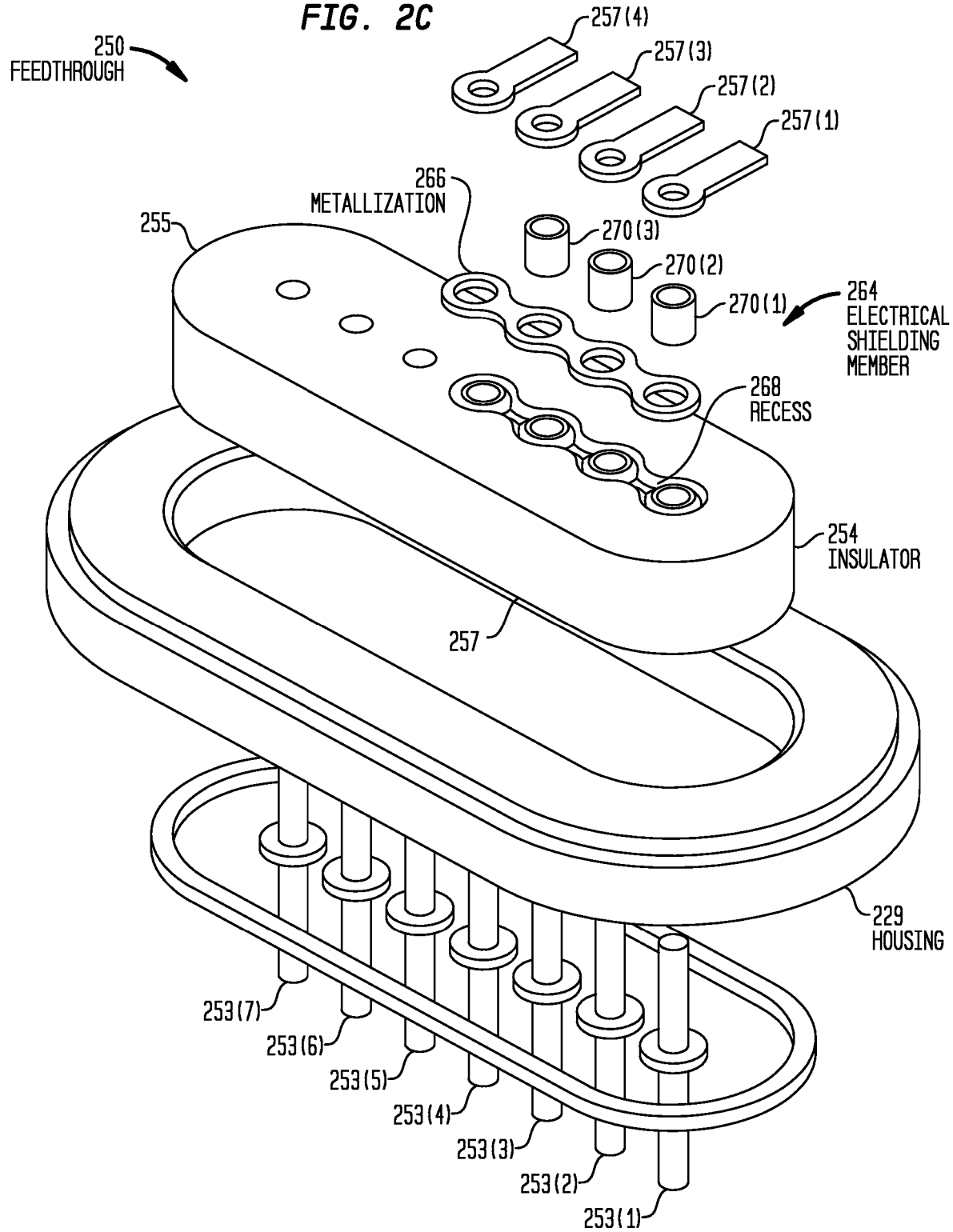

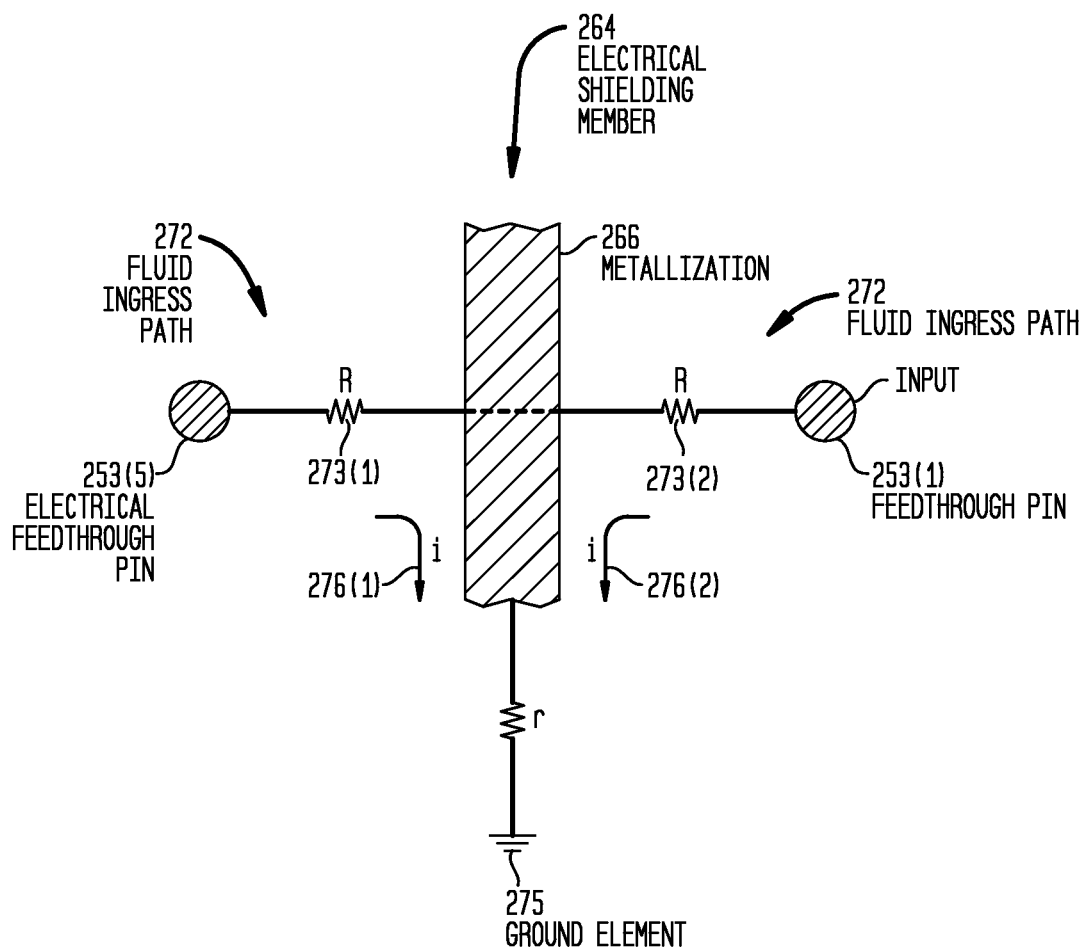

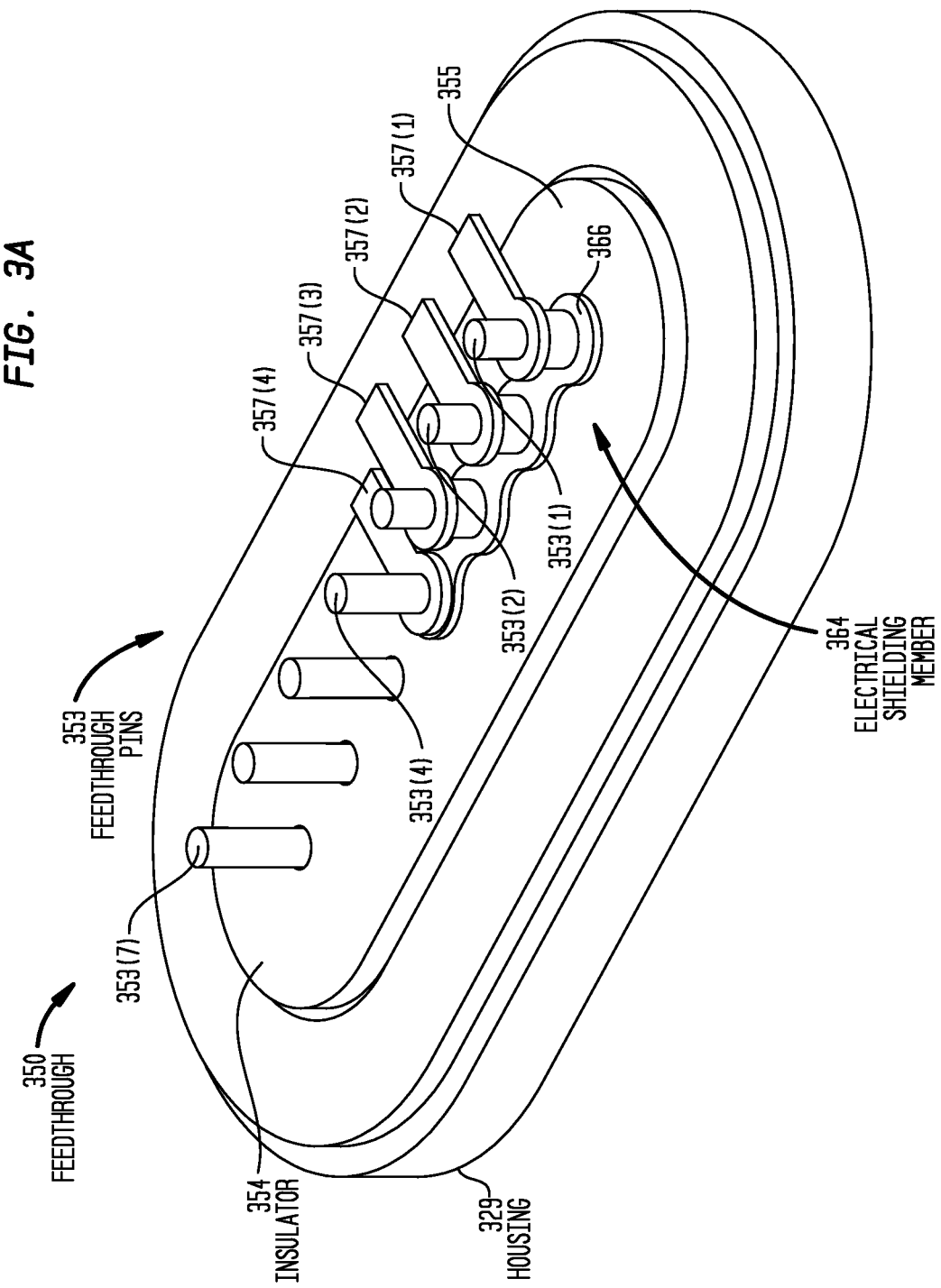

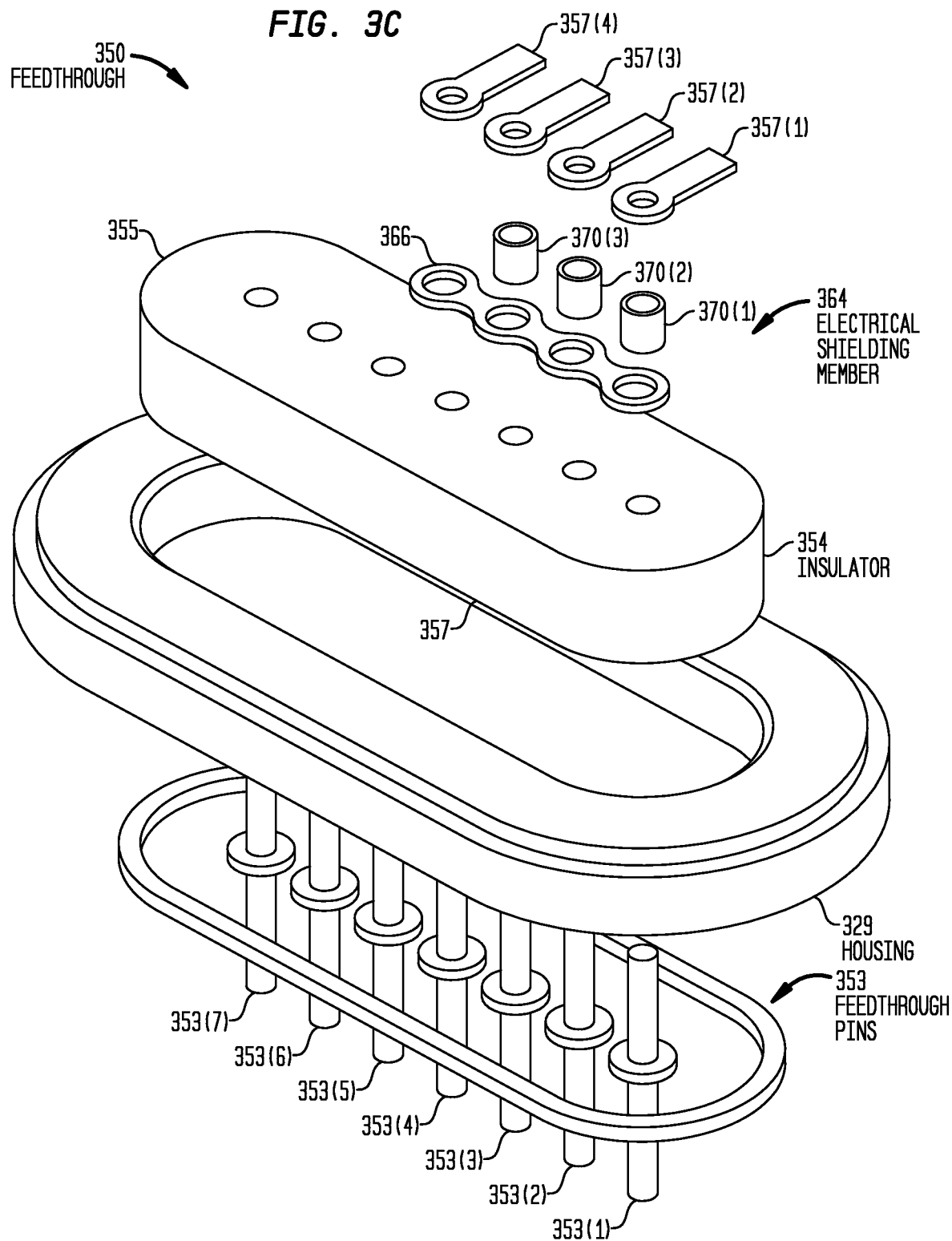

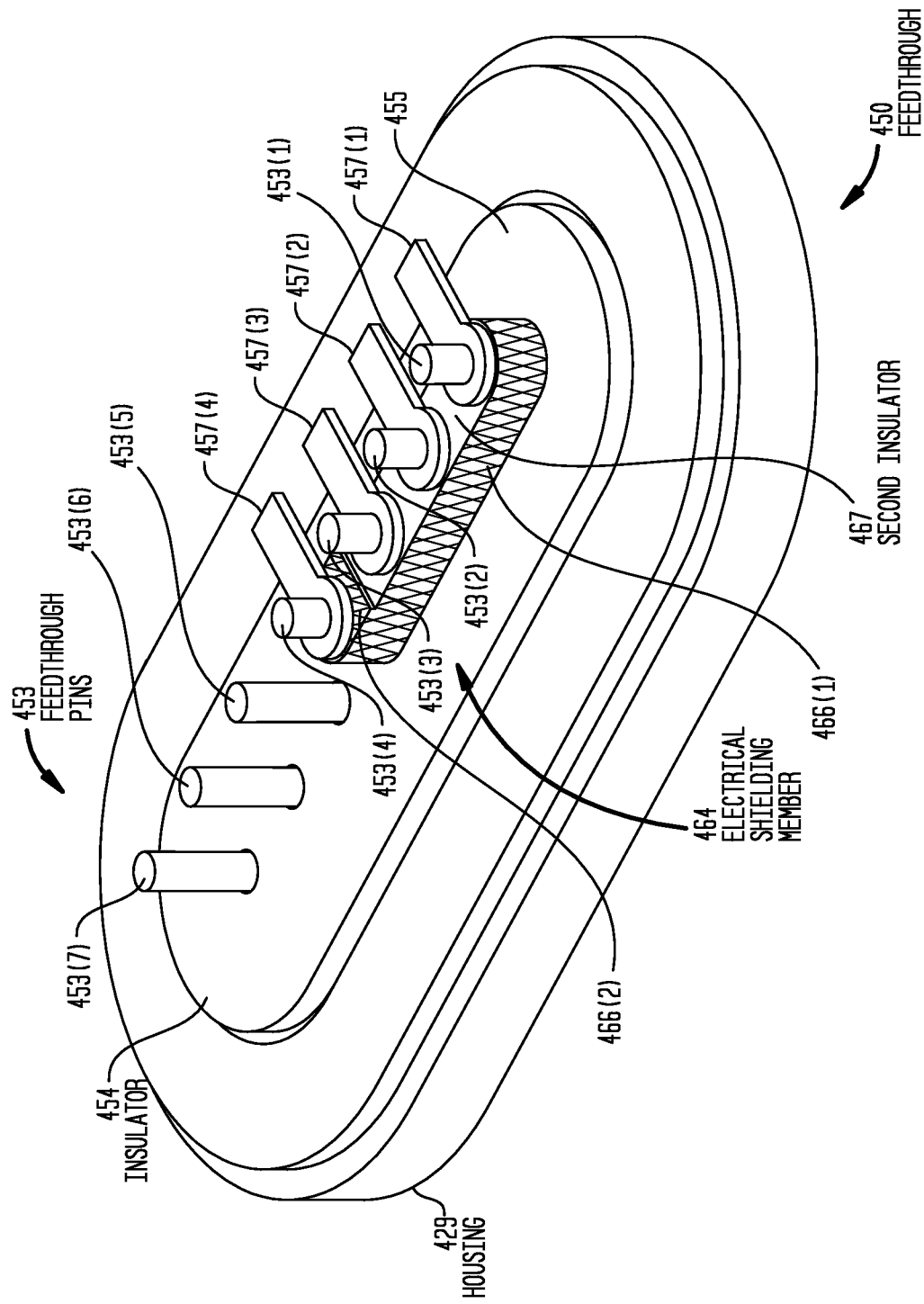

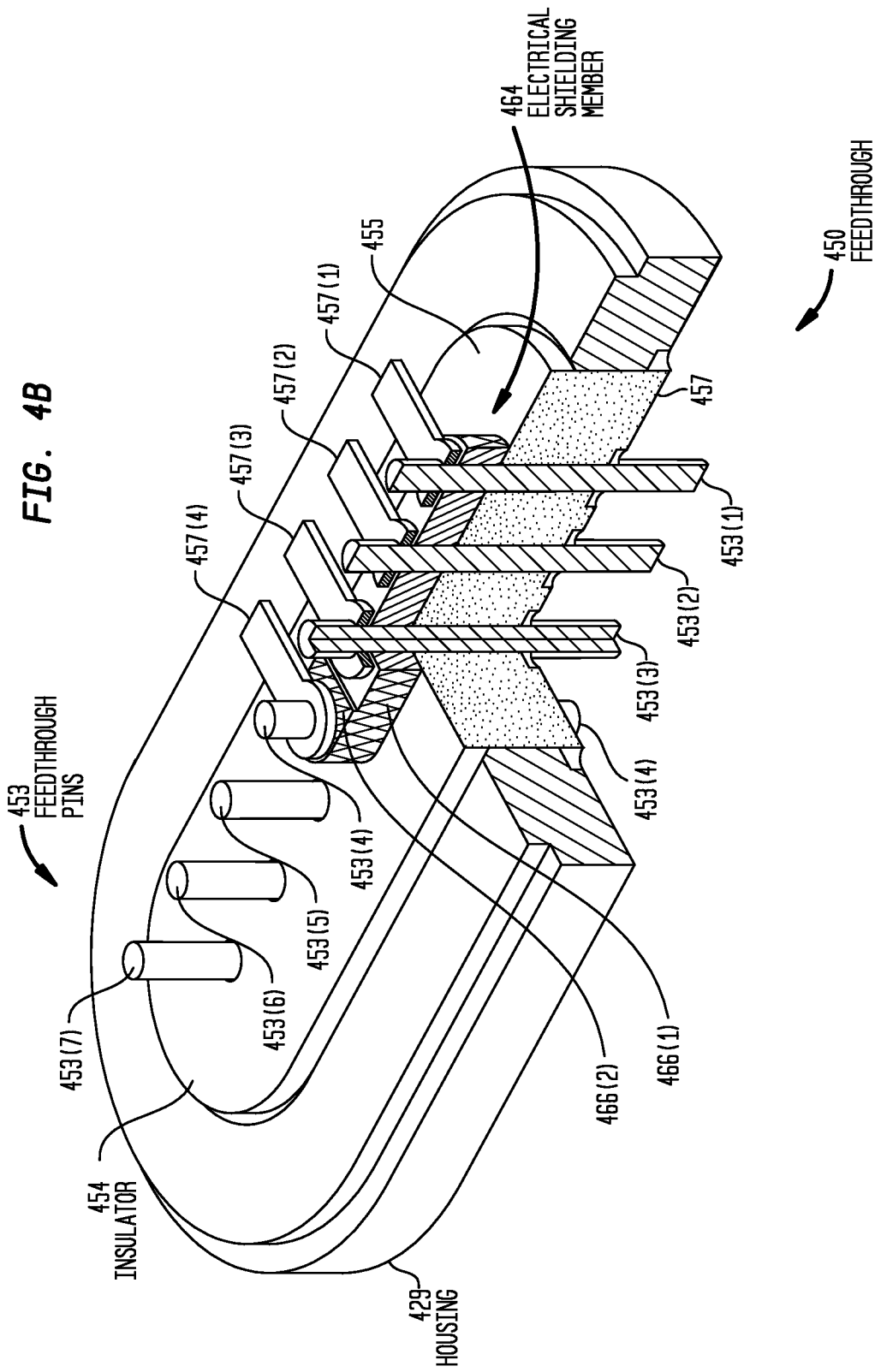

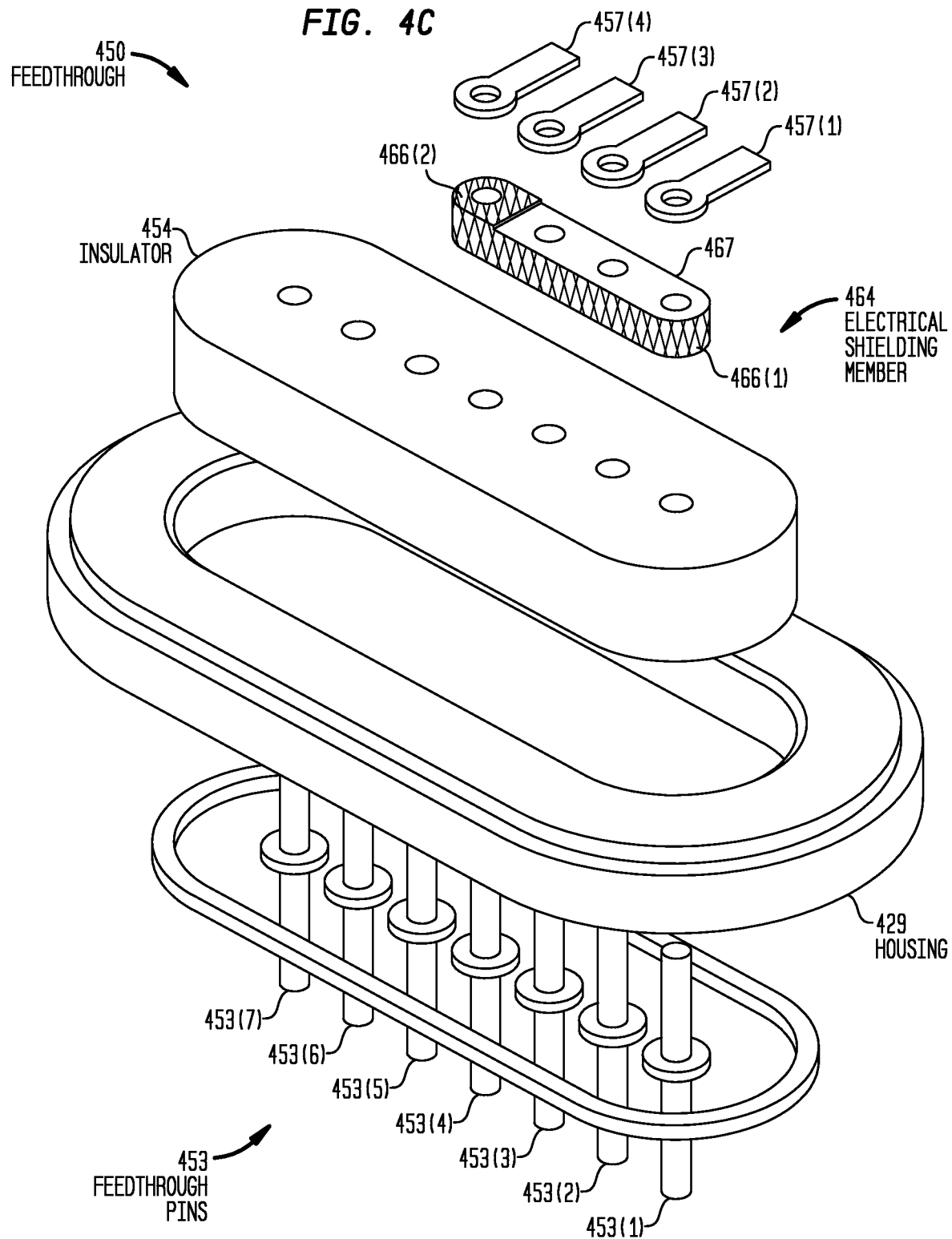

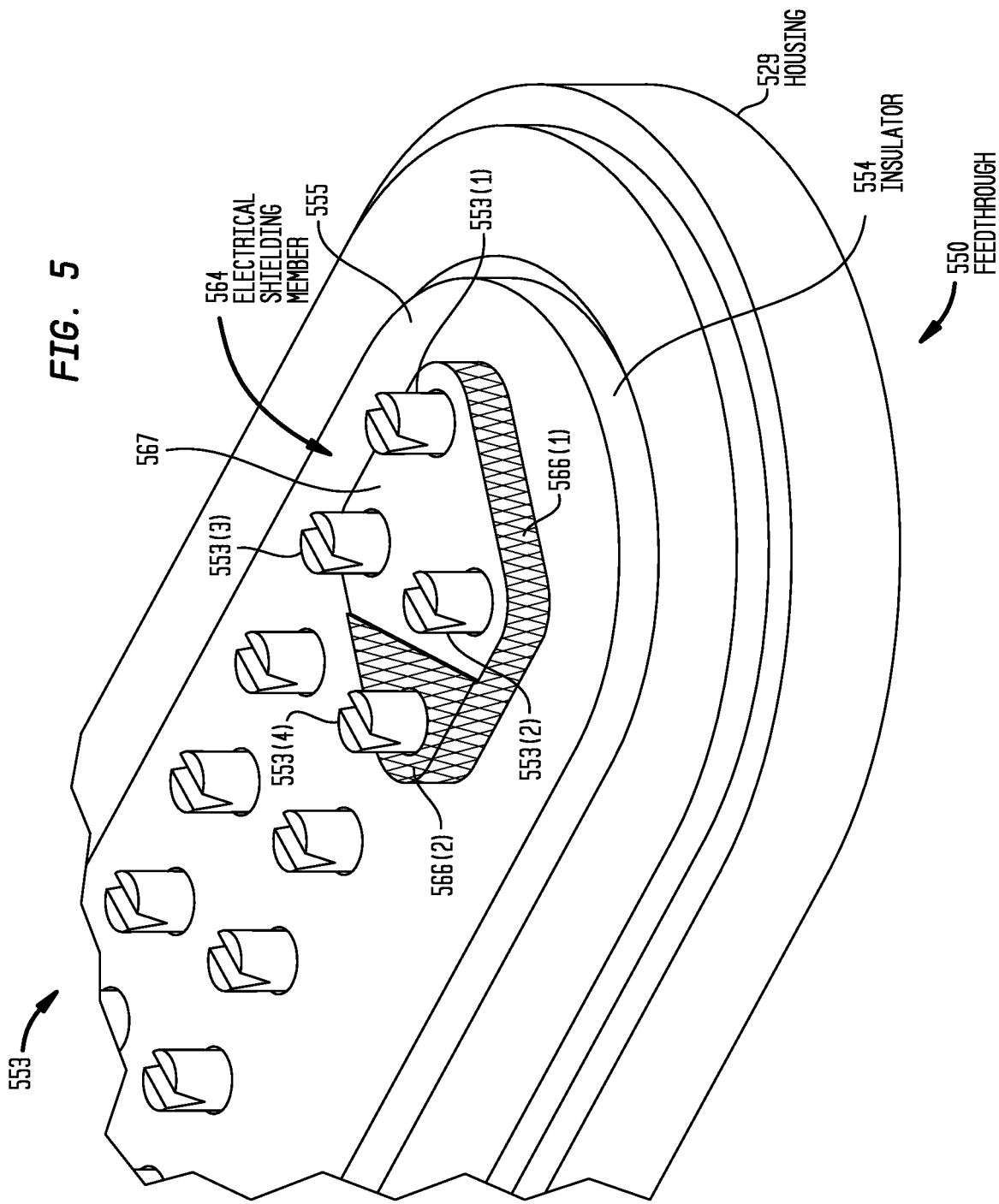

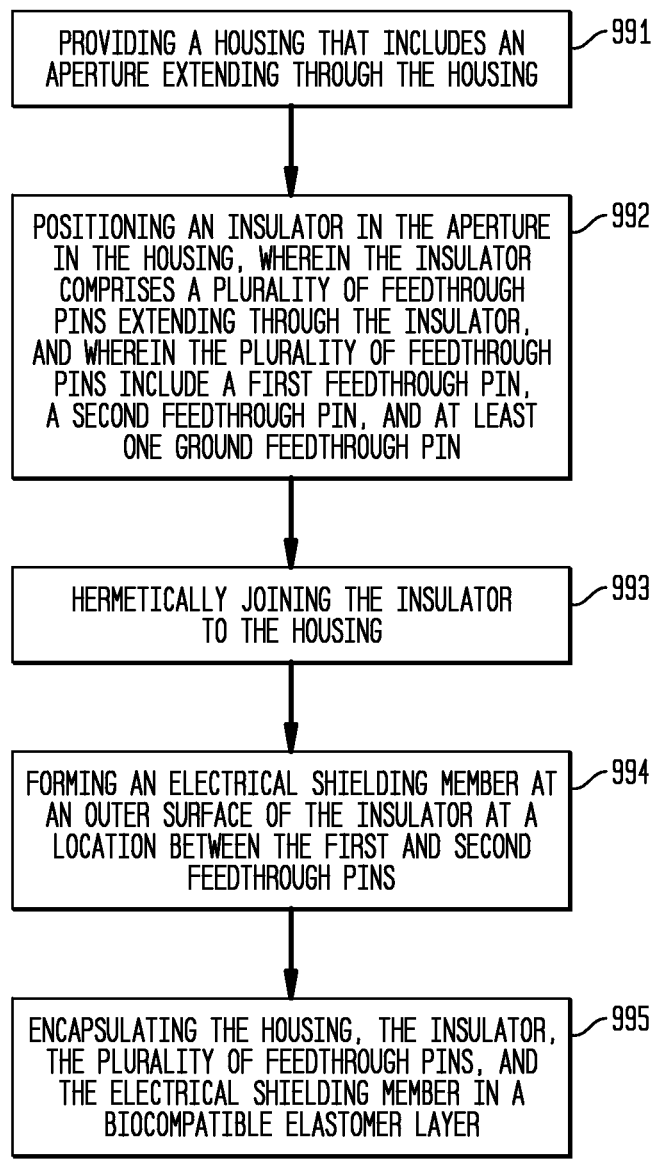

ELECTRICAL SHIELDING IN IMPLANTABLE MEDICAL DEVICES

BACKGROUND

Field of the Invention

Certain embodiments presented herein relate generally to shielding electrical signals from interference in implantable medical devices.

Related Art

Implantable medical devices, which include one or more implantable components, have provided a wide range of therapeutic benefits to recipients over recent decades. The types of implantable medical devices, as well as the range of functions performed thereby, have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify the anatomy or of a physiological process.

There are several types of implantable medical devices that operate by delivering electrical stimulation (current stimulation) to the nerves, muscle or other tissue fibers of a recipient. These implantable medical devices, sometimes referred to herein as implantable tissue-stimulating systems, typically deliver current stimulation to compensate for a deficiency in the recipient. For example, tissue-stimulating hearing systems (e.g., cochlear implants, auditory brainstem stimulators, etc.) are often proposed when a recipient experiences sensorineural hearing loss due to, for example, the absence or destruction of the cochlea hair cells that transduce acoustic signals into nerve impulses or when a recipient experiences sensorineural hearing loss due to damage to the auditory nerve.

SUMMARY

In one aspect, an implantable medical device is provided. The implantable medical device comprises: a hermetically-sealed biocompatible housing configured to be implanted in a recipient; an insulator extending through the housing, wherein the insulator comprises an outer surface that is external to the housing; a first feedthrough pin extending through the insulator and configured to carry first signals between a first functional component external to the housing and electronics within the housing; a second feedthrough pin extending through the insulator configured to carry second signals between a second functional component external to the housing and the electronics within the housing; and an electrical shielding member positioned on the outer surface of the insulator, wherein the electrical shielding member is configured to provide a grounding barrier between the first and second feedthrough pins.

In another aspect, a method is provided. The method comprises: providing a housing that includes an aperture extending through the housing; positioning an insulator in the aperture in the housing, wherein the insulator comprises a plurality of feedthrough pins extending through the insulator, and wherein the plurality of feedthrough pins include a first feedthrough pin, a second feedthrough pin, and at least one ground feedthrough pin; hermetically joining the insulator to the housing; forming an electrical shielding member at an outer surface of the insulator at a location between the first and second feedthrough pins; and encapsulating the housing, the insulator, the plurality of feedthrough pins, and the electrical shielding member in a biocompatible elastomer layer.

In another aspect, an implantable medical device is provided. The implantable medical device comprises: a hermetically-sealed biocompatible housing that includes an aperture extending there through; an insulator positioning in the aperture in the housing and having an outer surface that is external to the housing; a plurality of feedthrough pins extending through the insulator, wherein the plurality of feedthrough pins include a first feedthrough pin, a second feedthrough pin, and at least one ground feedthrough pin; a conductive element disposed at the outer surface of the insulator surrounding at least the second feedthrough pin and electrically connected to the at least one ground feedthrough pin; and a biocompatible elastomer layer encapsulating the housing, the insulator, the plurality of feedthrough pins, and the conductive element.

BRIEF DESCRIPTION OF THE DRAWINGS

Embodiments of the present invention are described herein in conjunction with the accompanying drawings, in which:

FIG. 1B is a block diagram of the cochlear implant of FIG. 1A, in accordance with certain embodiments presented herein;

FIG. 2C is an exploded view of a portion of feedthrough and electrical shielding member, in accordance with certain embodiments presented herein.

FIG. 2D is a schematic diagram illustrating operation of an electrical shielding member, in accordance with certain embodiments presented herein.

FIG. 3A is a perspective view of a portion of feedthrough and electrical shielding member, in accordance with certain embodiments presented herein.

FIG. 3C is an exploded view of a portion of feedthrough and electrical shielding member, in accordance with certain embodiments presented herein.

FIG. 4A is a perspective view of a portion of feedthrough and electrical shielding member, in accordance with certain embodiments presented herein.

FIG. 4B is a sectional view of a portion of feedthrough and electrical shielding member, in accordance with certain embodiments presented herein.

FIG. 4C is an exploded view of a portion of feedthrough and electrical shielding member, in accordance with certain embodiments presented herein.

FIG. 5 is a perspective view of a portion of feedthrough and electrical shielding member, in accordance with certain embodiments presented herein.

FIG. 9 is a flowchart of a method in accordance with certain embodiments presented herein.

DETAILED DESCRIPTION

Certain embodiments of the present invention are generally directed to techniques for electrically isolating pins of a hermetic feedthrough from one another. More specifically, in accordance with certain embodiments presented herein, an implantable medical device includes an insulator extending through a hermetically-sealed biocompatible housing. A plurality of feedthrough pins, which include at least a first feedthrough pin, a second feedthrough pin, and at least one ground feedthrough pin extend through the insulator. An electrically shielding member is disposed at the outer surface of the insulator surrounding at least the second feedthrough pin and is electrically connected to the at least one ground feedthrough pin. As such, the electrically shielding member provides a grounding barrier between the first and second feedthrough pins.

There are a number of different types of implantable medical devices in which certain embodiments of the present invention may be implemented. However, merely for ease of illustration, the techniques presented herein are primarily described with reference to one type of implantable medical device, namely a totally/fully implantable cochlear implant. However, it is to be appreciated that the techniques presented herein may be implemented by other implantable hearing prostheses, including auditory brainstem stimulators, electro-acoustic hearing prostheses, bimodal hearing prostheses, etc., and/or other types of implantable medical devices, such as implantable pacemakers, defibrillators, functional electrical stimulation devices, pain relief stimulators, visual prostheses, other neural or neuromuscular stimulators, etc.

Figure 1A:
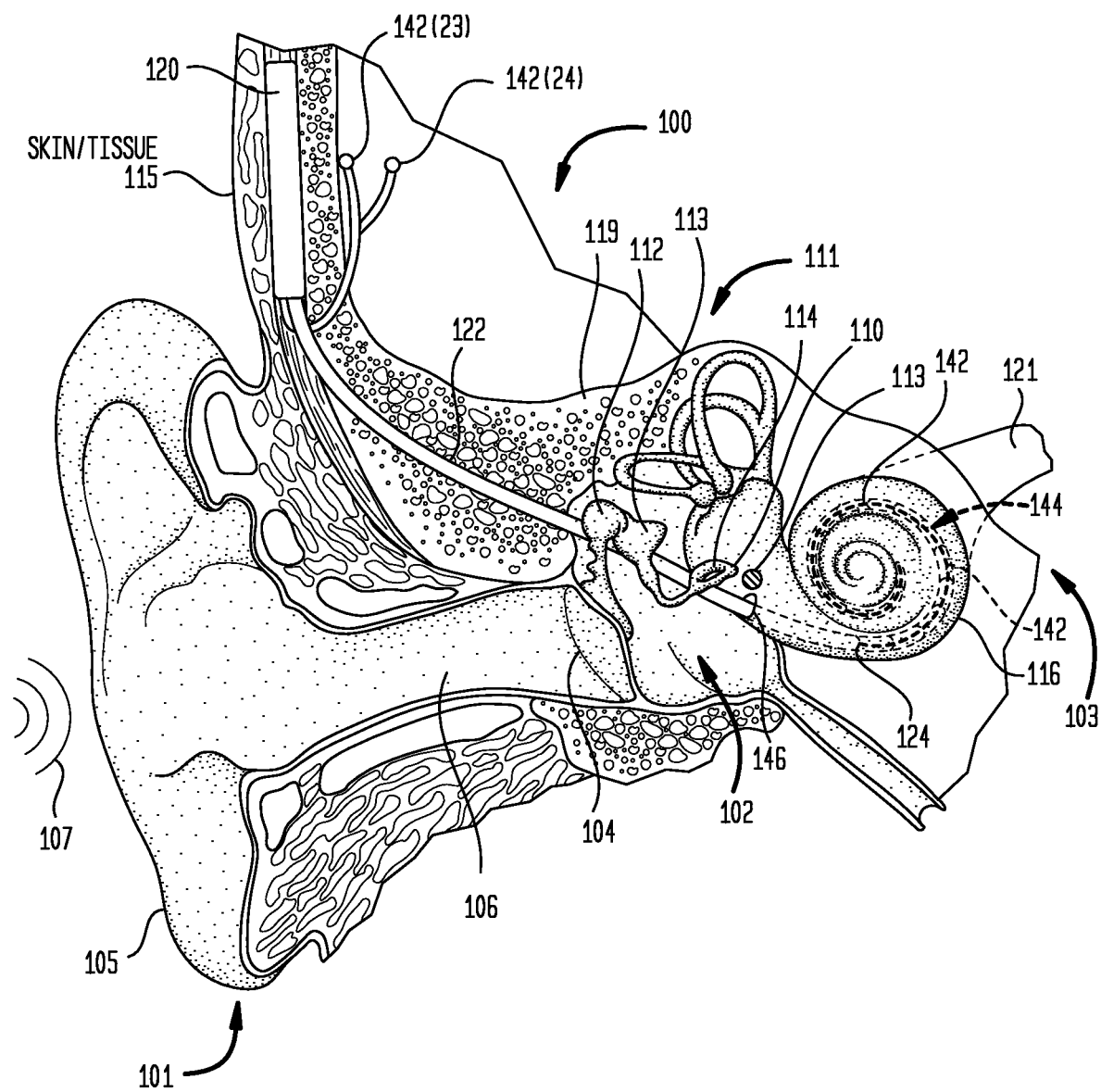
FIG. 1A is a schematic diagram illustrating a cochlear implant, in accordance with certain embodiments presented herein.

FIG. 1A is schematic diagram of an exemplary totally/fully cochlear implant 100 configured to implement certain embodiments presented herein, while FIG. 1B is a block diagram illustrating further details of the cochlear implant 100. For ease of description, FIGS. 1A and 1B will be described together.

Shown in FIG. 1A is an outer ear 101, a middle ear 102 and an inner ear 103 of the recipient. In a fully functional human hearing anatomy, the outer ear 101 comprises an auricle 105 and an ear canal 106. Sound signals 107, sometimes referred to herein as acoustic sounds or sound waves, are collected by the auricle 105 and channeled into and through the ear canal 106. Disposed across the distal end of the ear canal 106 is a tympanic membrane 104 which vibrates in response to the sound signals (i.e., sound waves) 107. This vibration is coupled to the oval window or fenestra ovalis 110 through three bones of the middle ear 102, collectively referred to as the ossicular chain or ossicles 111 and comprising the malleus 112, the incus 113 and the stapes 114. The ossicles 111 of the middle ear 102 serve to filter and amplify the sound signals 107, causing oval window 110 to vibrate. Such vibration sets up waves of fluid motion within the cochlea 116 which, in turn, activates hair cells (not shown) that line the inside of the cochlea 116. Activation of these hair cells causes appropriate nerve impulses to be transferred through the spiral ganglion cells and the auditory nerve 118 to the brain (not shown), where they are perceived as sound.

As noted above, sensorineural hearing loss may be due to the absence or destruction of the cochlea hair cells, which transduce acoustic signals into nerve impulses. One treatment for such hearing loss is a cochlear implant, such as cochlear implant 100 shown in FIGS. 1A and 1B, which bypasses the cochlear hair cells and delivers stimulation (e.g., electrical stimulation) directly to the cochlea nerve cells.

In the illustrative embodiment of FIGS. 1A and 1B, the cochlear implant 100 is a "totally implantable" cochlear implant, meaning that all components of the cochlear implant are configured to be implanted under skin/tissue 115 of a recipient. Because all components of cochlear implant 100 are implantable, the cochlear implant operates, for at least a finite period of time, without the need of an external device. An external device can be used to, for example, charge an internal power source (battery) of the cochlear implant 100.

The cochlear implant 100 comprises an implant body or main module 120, a lead region 122, and an elongate intra-cochlear stimulating assembly 124. The implant body 120 comprises a hermetically sealed housing 129 in which radio frequency (RF) interface circuitry 132 (sometimes referred to as a transceiver unit), at least one rechargeable battery 134, an implant controller 135, a sound processing unit 136, and a stimulator unit 138 are disposed. The housing 129 operates as a protective barrier between the electrical components within the housing (e.g., in RF interface circuitry 132, battery 134, etc.) and the recipient's tissue and bodily fluid. For ease of illustration, electrical connections between the components within housing 129 have been omitted from FIG. 1B.

The implant body 120 also comprises one or more electrical components located outside (external to) the housing 129. The electrical components located outside the housing 129 include an internal/implantable coil 130, implantable sound sensors/transducers 140(A) and 140(B), and the elongate intra-cochlear stimulating assembly 124.

The RF interface circuitry 132 is connected to the implantable coil 130 and, generally, a magnet (not shown) is fixed relative to the implantable coil 130. Implantable coil 130 is typically a wire antenna coil comprised of multiple turns of electrically insulated single-strand or multi-strand platinum or gold wire. In general, the implantable coil 130 and the RF interface circuitry 132 enable the transfer of power and/or data from an external device to the cochlear implant 100. However, it is to be appreciated that various types of energy transfer, such as infrared (IR), electromagnetic, capacitive and inductive transfer, may be used to transfer power and/or data from an external device to a cochlear implant 100 and, as such, FIG. 1B illustrates only one example arrangement.

As noted above, the cochlear implant 100 comprises two implantable sound sensors 140(A) and 140(B). In the illustrative embodiment of FIG. 1B, the implantable sound sensor 140(A) is a sensor/transducer that is primarily configured to detect/receive external acoustic sounds (e.g., an implantable microphone), while the implantable sound sensor 140(B) is a sound sensor that is primarily configured to detect/receive internal body noises (e.g., another implantable microphone or an accelerometer which is configured to be more sensitive to body noises than it is to external acoustic sound signals). Body noises (BNs) are undesirable sounds induced by the body that are propagated primarily as vibration, such as breathing, scratching, rubbing, noises associated with the movement of the head, chewing, own voice (OV), etc. For ease of description, certain embodiments presented herein will be primarily described with reference to the use of an implantable microphone 140(A) as the first sound sensor and an accelerometer 140(B) as the second sound sensor. However, it is to be appreciated that these specific implementations are non-limiting and that embodiments of the present invention may be used with a number of other different types of implantable sensors. For example, a hearing prosthesis or other medical device may also include other types of sensors, such as a telecoil, sensors for picking up nerve signals (e.g., an electroencephalogram (EEG)), etc. As such, the microphone 140(A) and the accelerometer 140(B) are merely illustrative of a number of different types of implantable elements configured to generate signals that are susceptible to interference/feedback in an implanted environment, as described elsewhere herein.

Elongate stimulating assembly 124 is configured to be at least partially implanted in cochlea 116 and extends through an opening in the cochlea 116 (e.g., cochleostomy 146, oval window 110, the round window 113, etc.). The stimulating assembly 124 has a proximal end connected to stimulator unit 138 via lead region 122 that extends through mastoid bone 119. Lead region 122 couples the stimulating assembly 124 to implant body 120 and, more particularly, to stimulator unit 138.

The stimulating assembly 124 includes a plurality of longitudinally spaced intra-cochlear electrical stimulating electrodes (electrodes) 142 that can be selectively used to deliver current to the cochlea 116. The stimulating electrodes 142 collectively form an intra-cochlear electrode array 144 that, in the example of FIG. 1B, comprises twenty-two (22) stimulating electrodes, labeled as electrodes 142(1)-142(22). Although FIG. 1B illustrates the use of twenty-two stimulating electrodes, is to be appreciated that different numbers, arrangements, etc., of intra-cochlear electrodes may be used in alternative embodiments.

Also shown in FIGS. 1A and 1B are two reference electrodes 142(23) and 142(24). The reference electrodes 142(23) and 142(24) are located outside of the cochlear 116 and can also be used to deliver current to the recipient. Since the reference electrodes 142(23) and 142(24) are located outside of the cochlea 116, the reference electrodes are sometimes referred to as extra-cochlear electrodes (ECEs).

In operation, the microphone 140(A) and/or the accelerometer 140(B) detect sound signals (e.g., external acoustic sounds and/or body noises) and convert the detected sound signals into analog electrical signals. The electrical signals generated by the microphone 140(A) and the accelerometer 140(B) are provided to the sound processing unit 136. The sound processing unit 136 is configured to execute signal processing and coding to convert the electrical signals into processed signals that represent the detected sound signals. The sound processing unit 136 is then configured to initiate generation of stimulation signals for delivery to the recipient via at least one output channel by providing the processed signals to the stimulator unit 138. The stimulator unit 138 is configured to utilize the processed signals to generate electrical stimulation signals that are delivered to the recipient's cochlea via one or more of the intra-cochlear stimulating electrodes 142(1)-142(22) implanted in the recipient's cochlea 116. In this way, cochlear implant 100 stimulates the recipient's auditory nerve cells, bypassing absent or defective hair cells that normally transduce acoustic vibrations into neural activity As described in detail above, the cochlear implant 100 includes both implanted sound sensors (e.g., microphone 140(A) and accelerometer 140(B)) as well as implanted stimulation components (e.g., intra-cochlear electrodes 142(1)-142(22) and reference electrodes 142(23)-142(24)). The sound sensors are used to capture input sound signals (e.g., acoustic sounds, body noises, etc.), which in turn are used by the cochlear implant 100 to generate stimulation signals for delivery to the recipient. That is, the cochlear implant 100 is a totally implantable device that is configured to: (1) detect/receive sounds from within the recipient, (2) process the sounds, and (3) generate stimulation signals for delivery to the recipient to evoke perception of the sound signals. As such, the use of the implantable sound sensors 140(A) and 140(B) provide the recipient with the ability to have a truly "invisible" prosthesis (i.e., since there are no external components, the prosthesis is invisible to others).

As noted, the microphone 140(A) and the accelerometer 140(B), as well as other electrical components of the cochlear implant 100, are located outside the hermetic housing 129. There is a need to enable electrical connections between these various components outside of the hermetic housing 129 with the various components within the housing 129. As such, the cochlear implant 100 includes a hermetic feedthrough 150 that provides a physical electrical connection that is used to transfer signals to/from the electrical components outside of the hermetic housing 129 to/from the electrical components within the hermetic housing 129.

Hermetic feedthroughs may be one of the more complex mechanical structures in an implantable medical device and are often difficult to form properly. Hermetic feedthrough 150, for example, generally includes an insulator 154 (e.g., formed from ceramic) and a plurality of conductive paths or "feedthrough pins" 153 that extend through the insulator. That is, the feedthrough pins 153 extend from an outer (non-hermetic) surface 155 of the insulator 154 (sometimes referred to herein as the outer surface 155 of feedthrough 150) to an inner surface 157 of the insulator 154. At the outer surface 155 of the insulator 154, the feedthrough pins 153 are exposed and can each be electrically connected (e.g., soldered, ultrasonically welded, etc.) to conductors 152. The conductors 152 electrically connect various one or more of the feedthrough pins 153 to one of the internal coil 130, microphone 140(A), accelerometer 140(B), reference electrode 142(23), reference electrode 142(24), and/or the intra-cochlear stimulating electrodes 142(1)-142(22). For ease of illustration, FIG. 1B illustrate only a subset of the intra-cochlear stimulating electrodes 142(1)-142(22) and, accordingly, only a subset of the conductors 152 extending to the intra-cochlear stimulating electrodes 142(1)-142(22).

Prior to implantation into a recipient, the housing 129, the internal coil 130, the feedthrough 150, and at least a portion of the conductors 152 in proximity to the outer surface 155 of the feedthrough 150 may be overmolded/encapsulated with a silicone elastomer 151 to create a uniform compliant surface suitable for implantation. For ease of illustration, the encapsulation 151 has been omitted from FIG. 1A and has been partially omitted form FIG. 1B, particularly around the feedthrough 150, the conductors 152, and feedthrough pins 153.

The encapsulation 151 generally isolates the conductors 152 and feedthrough pins 153 in proximity to the outer surface 155 of feedthrough 150 from each other and from the implanted environment. That is, the encapsulation is generally resistant to the ingress of bodily fluid and has material properties that electrically isolate the electrical connections. At the outer surface 155 of the hermetic feedthrough 150, only the applied encapsulation isolates the conductors 152 and/or the feedthrough pins 153.

It has been discovered that the encapsulation applied to medical devices may be susceptible to fluid ingress/leakage (i.e., the accumulation of conductive fluid on the outer surface 155 of the insulator 154, which bridges two feedthrough pins 153 and/or bridges the feedthrough pins to the housing 129, causing electrical leakage. That is, while the encapsulation provides a high impedance insulation between the feedthrough pins 153, over time body fluids can leak under the encapsulation on the outside of the feedthrough 150. This electrical leakage may be problematic when certain feedthrough pins 153 carry signals (e.g., low voltage analog signals) that are susceptible to noise and interference from signals (e.g., high voltage signals) carried by other feedthrough pins 153.

More specifically, fluid ingress into the encapsulation at the feedthrough 150 can lead to the creation of conductive "leakage paths" between the feedthrough pins 153 that connected to the input components (e.g., internal coil 130, microphone 140(A), accelerometer 140(B), etc.) and the feedthrough pins 153 that are connected to the output components (e.g., electrodes 142(1)-142(24)). In general, stimulation signals delivered to the electrodes 142(1)-142(24) have magnitudes that are significantly larger than the magnitudes of input signals received from the on the input components, such as the internal coil 130, microphone 140(A), accelerometer 140(B), etc. That is, certain feedthrough pins 153 carry high voltage stimulation signals (e.g., up to the order of 10 Volts) while other feedthrough pins 153 carry low voltage input signals (e.g., on the order of several millivolts). Due to this voltage difference, if a portion of the high voltage stimulation signals passes through a leakage path to another feedthrough pin 153 carrying an input signal, the portion of the high voltage signals will cause electrical interference within the input signal. In certain embodiments, this electrical interference may be perceived by the recipient as audible noise. In FIG. 1B, the presence of any number of leakage paths is represented by arrow 162.

Certain embodiments presented are directed to techniques for addressing/remediating the problems arising from the creation of conductive leakage paths at the outer surface of a hermetic feedthrough. More particularly, embodiments presented are directed to an electrical shielding member 164 at the outer surface 155 of the insulator 154. As described further below, the electrical shielding member 164 is positioned on the outer surface 155 so as to provide a grounding barrier between feedthrough pins 153 that carry signals that are susceptible to interference ("interference-susceptible signals") and feedthrough pins 153 that carry signals that are able to induce/cause interference ("interference-inducing signals").

The feedthrough pins 153 that carry interference-susceptible signals are sometimes referred to herein interference-susceptible feedthrough pins, while the feedthrough pins 153 that carry interference-inducing signals are sometimes referred to herein as interference-inducing feedthrough pins. Merely for purposes of illustration, certain embodiments will be described herein with reference to electrical shielding members, such as electrical shielding member 164, positioned between one specific type of interference-susceptible feedthrough pins, namely "input" feedthrough pins and one specific type of interference-inducing feedthrough pins, namely "electrode" feedthrough pins. As used herein, input feedthrough pins are pins that carry low voltage analog signals generated by implantable sound sensors (e.g., implantable microphones, accelerometers, telecoils, etc.), implantable coils, or other devices. Electrode feedthrough pins are pins that carry signals that have a voltage that is large compared to the low voltage analog signals, such as signals generated by a stimulator unit for delivery to a recipient via implanted electrodes. It is to be appreciated that the specific description of the embodiments presented herein with reference to input feedthrough pins and electrode feedthrough pins is illustrative and that electrical shielding members presented herein may also or alternatively be positioned between other types of feedthrough pins.

Figure 2A:
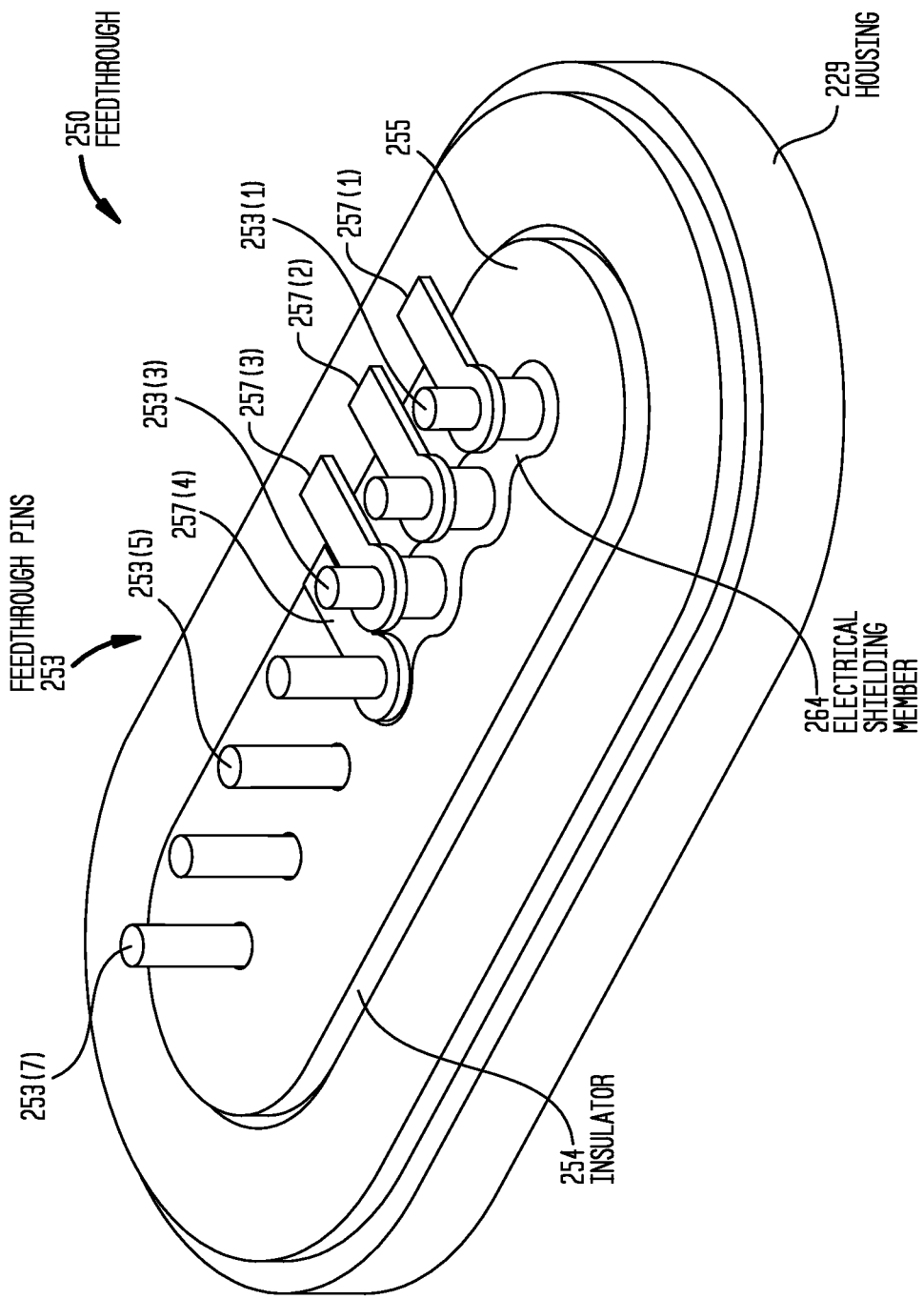
FIG. 2A is a perspective view of a portion of feedthrough and electrical shielding member, in accordance with certain embodiments presented herein.
Figure 2B:
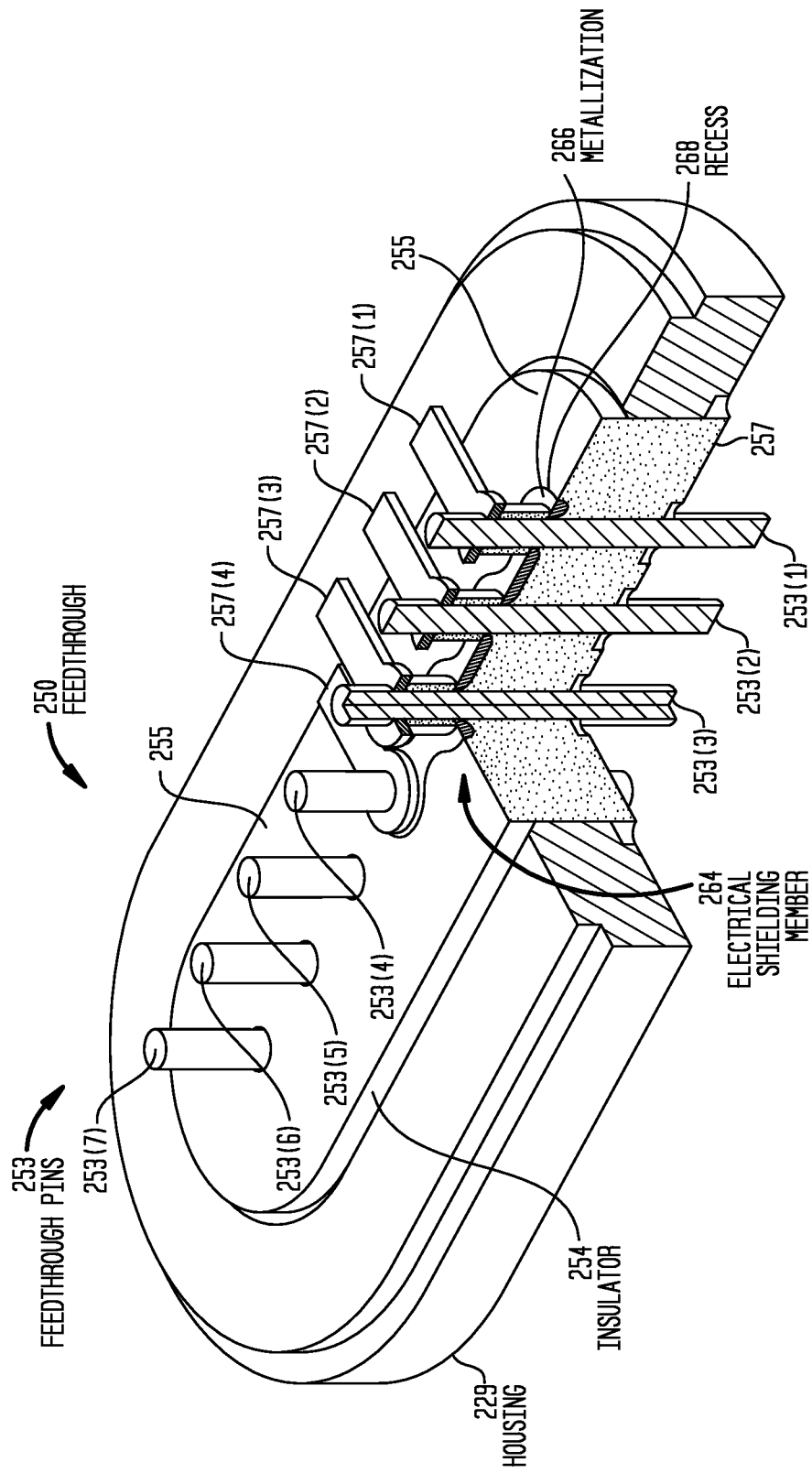
FIG. 2B is a sectional view of a portion of feedthrough and electrical shielding member, in accordance with certain embodiments presented herein.

FIGS. 2A, 2B, and 2C are diagrams illustrating a portion of a feedthrough 250 in accordance with certain embodiments presented herein. More specifically, FIG. 2A is a perspective view of the portion of the feedthrough 250, FIG. 2B is a sectional view of the feedthrough 250, and FIG. 2C is an exploded view of the feedthrough 250. For ease of illustration, the feedthrough 250 is shown in FIGS. 2A, 2B, and 2C without the presence of the encapsulation (i.e., the biocompatible elastomer layer has been omitted from FIGS. 2A-2C). Although FIGS. 2A-2C illustrate an elliptically-shaped feedthrough, it is to be appreciated that embodiments presented herein may be implemented with feedthroughs having different shapes. For ease of description, FIGS. 2A-2C will be described together.

The feedthrough 250 comprises an insulator 254 that extends through an aperture/opening in a housing 229 of a hearing prosthesis (e.g., cochlear implant). The housing 229 may be formed from, for example, titanium, platinum, or another biocompatible material. The feedthrough 250 also comprises a plurality of feedthrough pins 253 that extend through insulator 254 from an outer (non-hermetic) surface 255 of the insulator 254 (sometimes referred to herein as the outer surface 255 of feedthrough 250) to an inner surface 257 of the insulator 254. In the embodiments of FIGS. 2A-2C, the feedthrough 250 includes seven (7) feedthrough pins, referred to as feedthrough pins 253(1), 253(2), 253(3), 253(4), 253(5), 253(6), and 253(7). It is to be appreciated that the inclusion of seven feedthrough pins is merely illustrative and that feedthroughs in accordance with certain embodiments presented herein may include different numbers of feedthrough pins.

In order to ensure that the housing 229 provides a hermetic seal between electrical components inside the housing 229 and the recipient's tissue and bodily fluid, the insulator 254 is hermetically attached/joined to the housing. As described further below, depending on the techniques used to form the insulator 254 and/or the feedthrough pins 253, the insulator 254 may be attached to the housing 229 in a number of different manners.

For example, in certain embodiments, the insulator 254 is hermetically joined to the housing 229 through brazing. Brazing is a joining process where braze metal (e.g., titanium-copper-nickel foil (TiCuNi), gold, etc.) is heated above its melting point so as to be distributed between two or more close-fitting parts (e.g., the housing 229 and the insulator 254). After the braze material flows between the insulator 254 and the housing 229, the braze material is cooled so as to harden and hermetically join the insulator 254 to the housing 229. In these examples, the insulator 254 is a monolithic ceramic element that is formed around the feedthrough pins 253 that comprise wires or other continuous conductive elements.

In other embodiments, the insulator 254 and the feedthrough pins 253 are formed through a layering process.

That is, the insulator 254 is comprised of a plurality of layers of non-conductive material that are layered on top of one another, layer-by-layer. In these embodiments, the feedthrough pins 253 are formed by traces/tracks within each non-conductive material layer of the insulator 254, and the trace layers are interconnected with one another (i.e., interconnected traces forming the feedthrough pins that are formed layer-by-layer). In certain such examples, platinum paste is screen printed/stenciled onto a ribbon of ceramic (e.g., on a reel). This is built up in several layers, before the layered assembly is sintered together into a single assembly. This ceramic/platinum layered assembly is then brazed into a housing.

It is to be appreciated that the insulator 254 and the feedthrough 253 pins may not only be formed in a number of different manners, but also that the insulator 254 may be joined to the housing 229 in a number of different manners. Accordingly, the use of a monolithic insulator or the use of a multi-layer insulator are illustrative of the numerous techniques that may be used in accordance with certain embodiments presented herein to form the insulator 254 and/or join the insulator 254 to the housing 229.

As noted above, the feedthrough pins 253(1)-253(7) may be elongate wires (e.g., formed from platinum), interconnected traces, or other types of conductive pathways that pass electrical signals between electrical components located within the housing 229 and electrical components located outside of the housing 229. In the specific embodiments of FIGS. 2A-2C, feedthrough pins 253(1) and 253(2) are referred to as "input feedthrough" pins because they carry electrical signals (current) received at one or more implantable sound sensors (e.g., microphones, accelerometers, etc.) to components within the housing 229. Again, for ease of illustration, the one or more implantable sound sensors have been omitted from FIGS. 2A-2C. However, shown in FIGS. 2A-2C are portions of lead conductors 257(1) and 257(2) that may be used to electrically connect the one or more sound input elements to the feedthrough pins 253(1) and 253(2), respectively. The lead conductors 257(1) and 257(2) may be connected to the feedthrough pins 253(1) and 253(2), respectively, via gold brazing, conductive epoxy, solder, mechanical riveting, etc.

Feedthrough pin 253(3) is referred to as a "power pin" because it delivers operating power to the one or more implantable sound sensors, while the feedthrough pin 253(4) is referred to as a "ground pin." The ground pin 253(4) is electrically connected to a ground node/element of the hearing prosthesis via a low impedance electrical connection. The ground element is a component that serves as a zero voltage reference point within the hearing prosthesis, (i.e., a designated reference point against which other potentials in the circuit are measured, assigned a potential of zero volts). FIGS. 2A-2C also illustrate lead conductors 257(3) and 257(4) electrically connected (e.g., via gold brazing, conductive epoxy, etc.) to the feedthrough pins 253(3) and 253(4), respectively. These lead conductors 257(3) and 257(4) may be used to electrically connect the one or more sound input elements to the feedthrough pins 253(3) and 253(4), respectively.

In certain embodiments, the ground pin 253(4) may be a "common" ground pin that is connected to a "common ground element," while in other embodiments the ground pin 253(4) may be an "isolated" ground pin connected to an "isolated ground element." A common ground element is a ground element/node that is also used by the audio circuit of the hearing prosthesis. An isolated ground is a ground element that is electrically separated from the audio circuit.

In certain examples, since the isolated ground is the ground for a part of the hearing prosthesis that is different from the audio circuit, the isolated ground may be less likely to cause interference with the audio circuit. In certain common ground embodiments, the ground pin 253(4) may be electrically connected to the system ground.

Returning to the embodiments of FIGS. 2A-2C, as noted the feedthrough 250 also includes feedthrough pins 253(5), 253(6), and 253(7). In these embodiments, the feedthrough pins 253(5), 253(6), and 253(7) are electrically connected to implanted electrodes of the hearing prosthesis and, as such, carry electrical signals between the implanted electrodes and electrical components within housing 229. Accordingly, the feedthrough pins 253(5), 253(6), and 253(7) are referred to herein as "electrode feedthrough pins." For ease of illustration the electrodes, as well as the lead conductors for connection to the electrodes, have been omitted from FIGS. 2A-2C.

As shown in FIGS. 2A-2C, the feedthrough 250 has a compact design in which the input feedthrough pins 253(1) and 253(2) are located in relatively close proximity to the electrode feedthrough pins 253(5), 253(6), and 253(7). As noted, in conventional arrangements, fluid ingress into the encapsulation could lead to the formation of conductive fluid ingress/leakage paths between one or more of the electrode feedthrough pins and one or more of the input feedthrough pins. Also as noted above, the formation of a conductive fluid ingress path leads to the potential for interference one or more of the feedthrough pins. The embodiments of FIGS. 2A-2C remediate the effects of conductive fluid paths through the formation of an electrical shielding member (electrical ground shield) 264 at the outer surface 255 of the insulator 254. The electrical shielding member 264 is positioned at the outer surface 255 so as to provide a grounding barrier between the input feedthrough pins 253(1) and 253(2) (e.g., feedthrough pins 253 that carry interference-susceptible signals) and electrode feedthrough pins 253(5), 253(6), and 253(7) (e.g., feedthrough pins that carry interference-inducing signals).

It is to be noted that, although FIGS. 2A-2C, the feedthrough 250 having a compact design, fluid ingress may also be problematic in arrangements in which the feedthrough pins are located far away from each other. For example, even in more spaced arrangements (i.e., arrangements in which the feedthrough pins are located far away from each other), interference may occur when the fluid ingress bridge from an interfering pin to the housing, and then from the housing to the interference-susceptible pin.

In the embodiments of FIGS. 2A-2C, the electrical shielding member 264 comprises a conductive layer 266 that is disposed within a recessed area (recess) 268 formed in the outer surface 255 of the insulator 254. The conductor 266 may comprise, for example, a metallization that is applied within the recess 268 via, for example, with ion sputtering and masking, ion sputtering and post-machining, electroplating/electrodeposition, etc.

As shown, the recess 268, and accordingly the conductive layer 266 which is located in the recess 268, surround the input feedthrough pins 253(1) and 253(2), as well as the power pin 253(3) and the ground pin 254(4). The conductive layer 266 is electrically connected to the ground pin 253(4) (e.g., via gold brazing, conductive epoxy, solder, mechanical riveting, etc.), but is electrically separated from each of the input feedthrough pin 253(1), the input feedthrough pin 253(2), and the power pin 253(3) via insulating spacing elements (insulating spacers) 270(1), 270(2), and 270(3), respectively.

Since the conductive layer 266 surrounds the feedthrough pins 253(1)-253(4), the conductive layer 266 is physically located between the electrode pins 253(5)-253(7) and the feedthrough pins 253(1)-253(4). As such, any fluid ingress path that bridges between any of the feedthrough pins 253(5)-253(7) and any of the feedthrough pins 253(1)-253(4) will necessarily cross the electrical shielding member 264, namely the conductive layer 266 (i.e., the conductive layer 266 is it in intimate contact with surface of feedthrough surface where conductive fluid can accumulate, thus the conductive layer 266 is disposed in the fluid ingress path). Since, as noted, the conductive layer 266 is electrically connected to the ground pin 253(4) (and thus the ground element), any signals passing through the fluid ingress will be shorted to the ground element via the low impedance connection. Stated differently, the conductive layer 266 will short any signals passing thereto to the ground element of the hearing prosthesis, thereby shielding the input feedthrough pins 253(1) and 253(2) from interference (i.e., the electrical shielding member 264 makes the implantable sound sensors less susceptible to noise due to fluid ingress into the encapsulation at the feedthrough 250).

As such, FIGS. 2A-2C generally illustrate embodiments in which a recess 268 is machined into the outer surface 255 of the insulator 254 so as to surround at least the feedthrough pins 253(1) and 253(2) (i.e., the implantable sensor pins). Metallization 266 may be applied to a large portion of the outer surface 255 of the insulator 254 and any portions of the metallization 266 not located in the recess 268 is removed (e.g., via grinding), leaving only the metallization within the recess. Subsequently, the metallization 266 disposed in the recess 268 may be electrically connected to the ground pin 257(4).

FIG. 2D is a schematic diagram illustrating operation of the electrical shielding member 264 with reference to two example pins of feedthrough 250, namely electrode feedthrough 253(5) and input signal pin 253(1). In the example of FIG. 2D, a fluid ingress path 272, which is schematically represented by resistors 273(1) and 273(2), is formed at the outer surface 255 of the feedthrough 250. The resistors 273(1) and 273(2) indicate the fluid ingress path 272 has conductive properties such that electrical signals (current) can flow from the electrode feedthrough pin 253(5) towards the input feedthrough pin 253(1), or vice versa. However, as noted above, the electrical shielding member 264 is disposed within the fluid ingress path 272 (i.e., in intimate contact with surface of feedthrough ceramic where conductive fluid can accumulate). Also as noted above, the conductive layer 266 of the electrical shielding member 264 is electrically connected to a ground element of hearing prosthesis, schematically illustrated in FIG. 2D as ground element 275. As a result of the electrical connection of the conductive layer 266 to the ground element 275, electrical signals passing through the fluid ingress path 272 (either from the electrode feedthrough pin 253(5) towards the input feedthrough pin 253(1), or vice versa) will be shorted to the ground element 275. The electrical shorting of the electrical signals (current) passing through the fluid ingress path 272 is schematically illustrated in FIG. 2D by current arrows 276(1) and 276(2).

Current arrows 276(1) and 276(2) are shown on opposing sides of the electrical shielding member 264 to indicate that the shielding member operates as a bi-directional grounding barrier. More specifically, FIGS. 2A-2C have been primarily described with reference to certain embodiments in which the electrical shielding member 264 protects the input feedthrough pins 253(1) and 253(2) from the stimulation signals carried by the electrode feedthrough pins 253(5)-253(7). This protection is useful because the stimulation signals on the electrode feedthrough pins 253(5)-253(7) are orders of magnitude larger that the sound sensor signals carried by the input feedthrough pins 253(1) and 253(2) (e.g., the stimulation signals are to the order of 10 Volts while the sound sensor input signals are on the order of several millivolts). Due to this voltage difference, if a portion of the high voltage stimulation signals on electrode feedthrough pin 253(1) passes through the fluid ingress path 272, the portion of the voltage signals will cause electrical interference within the input signal on the input feedthrough pin 253(1).

However, it is also to be appreciated that, in certain arrangements, the electrode feedthrough pins 253(5)-253(7) may alternatively be used to obtain neural measurements from the implanted electrodes (i.e., carry measurement signals from the electrodes to the components within housing 229). The neural measurements may have low magnitudes which makes them susceptible to interference from, for example, power feedthrough pin 253(3), when a fluid ingress path is present. Since, as noted, the electrical shielding member 264 is a bi-directional grounding barrier, the electrical shielding member 264 is also able to protect the electrode feedthrough pins 253(5)-253(7) (when carrying neural measurements) from the power feedthrough pin 253(3) and/or the input feedthrough pins 253(1) and 253(2), as needed.

Figure 3B:
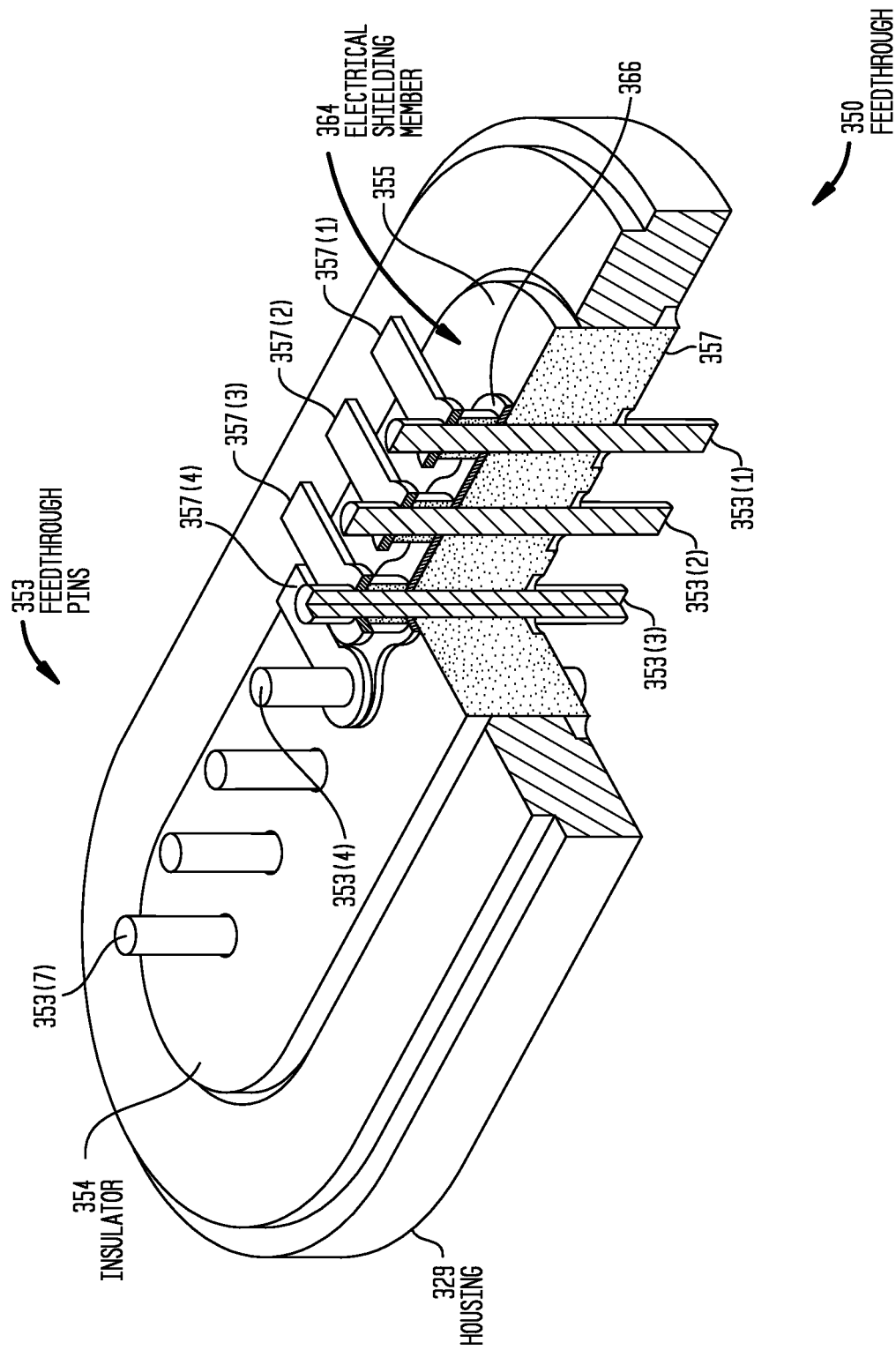
FIG. 3B is a sectional view of a portion of feedthrough and electrical shielding member, in accordance with certain embodiments presented herein.

FIGS. 3A, 3B, and 3C are diagrams illustrating a portion of a feedthrough 350 in accordance with certain embodiments presented herein. More specifically, FIG. 3A is a perspective view of the portion of the feedthrough 350, FIG. 3B is a sectional view of the feedthrough 350, and FIG. 3C is an exploded view of the feedthrough 350. For ease of illustration, the feedthrough 350 is shown in FIGS. 3A, 3B, and 3C without the presence of any encapsulation. Although FIGS. 3A-3C illustrate an elliptically-shaped feedthrough, it is to be appreciated that embodiments presented herein may be implemented with feedthroughs having different shapes. For ease of description, FIGS. 3A-3C will be described together.

The feedthrough 350 comprises an insulator 354 that extends through an opening in a housing 329 of a hearing prosthesis (e.g., cochlear implant). The housing 329 may be formed from, for example, titanium, platinum, or another biocompatible material. The feedthrough 350 also comprises a plurality of feedthrough pins 353 that extend through insulator 354 from an outer (non-hermetic) surface 355 of the insulator 354 (sometimes referred to herein as the outer surface 355 of feedthrough 350) to an inner surface 357 of the insulator 354. In the embodiments of FIGS. 3A-3C, the feedthrough 350 includes seven (7) feedthrough pins, referred to as feedthrough pins 353(1), 353(2), 353(3), 353(4), 353(5), 353(6), and 353(7). It is to be appreciated that the inclusion of seven feedthrough pins is merely illustrative and that feedthroughs in accordance with certain embodiments presented herein may include different numbers of feedthrough pins.

In order to ensure that the housing 329 provides a hermetic seal between electrical components inside the housing 329 and the recipient's tissue and bodily fluid, the insulator 354 is hermetically attached/joined to the housing. As described elsewhere herein, depending on the techniques used to form the insulator 354 and/or the feedthrough pins 353, the insulator 354 may be attached to the housing 329 in a number of different manners. In certain embodiments, the insulator 354 is a monolithic element that is hermetically joined to the housing 329 through brazing, as described elsewhere herein. In other embodiments, the insulator 354 and the feedthrough pins 353 are formed through a layering process, also as described elsewhere herein. It is to be appreciated that the use of a monolithic insulator or the use of a multi-layer insulator are illustrative of the numerous techniques that may be used in accordance with certain embodiments presented herein to form the insulator 354 and/or join the insulator 354 to the housing 329.

As noted above, the feedthrough pins 353(1)-353(7) may be elongate wires (e.g., formed from platinum), interconnected traces, or other types of conductive pathways that pass electrical signals between electrical components located within the housing 329 and electrical components located outside of the housing 329. In the specific embodiments of FIGS. 3A-3C, feedthrough pins 353(1) and 353(2) are referred to as "input feedthrough" pins because they carry electrical signals (current) received at one or more implantable sound sensors (e.g., microphones, accelerometers, etc.) to components within the housing 329. Again, for ease of illustration, the one or more implantable sound sensors have been omitted from FIGS. 3A-3C. However, shown in FIGS. 3A-3C are portions of lead conductors 357(1) and 357(2) that may be used to electrically connect the one or more sound input elements to the feedthrough pins 353(1) and 353(2), respectively. The lead conductors 357(1) and 357(2) may be connected to the feedthrough pins 353(1) and 353(2), respectively, via gold brazing, conductive epoxy, solder, mechanical riveting, etc.

Feedthrough pin 353(3) is referred to as a "power pin" because it delivers operating power to the one or more implantable sound sensors, while the feedthrough pin 353(4) is referred to as a "ground pin." The ground pin 353(4) is electrically connected to a ground node/element of the hearing prosthesis via a low impedance electrical connection. The ground element is a component that serves as a zero voltage reference point within the hearing prosthesis, (i.e., a designated reference point against which other potentials in the circuit are measured, assigned a potential of zero volts). FIGS. 3A-3C also illustrate lead conductors 357(3) and 357(4) electrically connected (e.g., via gold brazing, conductive epoxy, etc.) to the feedthrough pins 353(3) and 353(4), respectively. These lead conductors 357(3) and 357(4) may be used to electrically connect the one or more sound input elements to the feedthrough pins 353(3) and 353(4), respectively.

In certain embodiments, the ground pin 353(4) may be a "common" ground pin that is connected to a "common ground element," while in other embodiments the ground pin 353(4) may be an "isolated" ground pin connected to an "isolated ground element." A common ground element is a ground element/node that is also used by the audio circuit of the hearing prosthesis. An isolated ground is a ground element that is electrically separated from the audio circuit. In certain examples, since the isolated ground is the ground for a part of the hearing prosthesis that is different from the audio circuit, the isolated ground may be less likely to cause interference with the audio circuit. In certain common ground embodiments, the ground pin 353(4) may be electrically connected to the system ground.

Returning to the embodiments of FIGS. 3A-3C, as noted the feedthrough 350 also includes feedthrough pins 353(5), 353(6), and 353(7). In these embodiments, the feedthrough pins 353(5), 353(6), and 353(7) are electrically connected to implanted electrodes of the hearing prosthesis and, as such, carry electrical signals between the implanted electrodes and electrical components within housing 329. Accordingly, the feedthrough pins 353(5), 353(6), and 353(7) are referred to herein as "electrode feedthrough pins." For ease of illustration the electrodes, as well as the lead conductors for connection to the electrodes, have been omitted from FIGS. 3A-3C.

As shown in FIGS. 3A-3C, the feedthrough 350 has a compact design in which the input feedthrough pins 353(1) and 353(2) are located in relatively close proximity to the electrode feedthrough pins 353(5), 353(6), and 353(7). As noted, in conventional arrangements, fluid ingress into the encapsulation could lead to the formation of conductive fluid ingress/leakage paths between one or more of the electrode feedthrough pins and one or more of the input feedthrough pins. Also as noted above, the formation of a conductive fluid ingress path leads to the potential for interference one or more of the feedthrough pins. The embodiments of FIGS. 3A-3C remediate the effects of conductive fluid paths through the formation of an electrical shielding member (electrical ground shield) 364 at the outer surface 355 of the insulator 354. The electrical shielding member 364 is positioned at the outer surface 355 so as to provide a grounding barrier between the input feedthrough pins 353(1) and 353(2) (e.g., feedthrough pins 353 that carry interference-susceptible signals) and electrode feedthrough pins 353(5), 353(6), and 353(7) (e.g., feedthrough pins that carry interference-inducing signals).

In the embodiments of FIGS. 3A-3C, the electrical shielding member 364 comprises a conductive layer 366 that is disposed on the outer surface 355 of the insulator 354. In certain embodiments, the conductive layer 366 may comprise a selectively applied metallization (e.g., a metallization applied via ion sputtering and masking, ion sputtering and post-machining, electroplating/electrodeposition, etc.). In other embodiments, the conductive layer 366 may comprise a metal foil element or wire that is attached/adhered to the outer surface 355 of the insulator 354 via, for example, conductive epoxy, conductive silicone, or other conductive bonding agent.

As shown, the conductive layer 366 surrounds the input feedthrough pins 353(1) and 353(2), as well as the power pin 353(3) and the ground pin 354(4). The conductive layer 366 is electrically connected to the ground pin 353(4) (e.g., via gold brazing, conductive epoxy, solder, mechanical riveting, etc.), but is electrically separated from each of the input feedthrough pin 353(1), the input feedthrough pin 353(2), and the power pin 353(3) via insulating spacing elements (insulating spacers) 370(1), 370(2), and 370(3), respectively.

Since the conductive layer 366 surrounds the feedthrough pins 353(1)-353(4), the conductive layer 366 is physically located between the electrode pins 353(5)-353(7) and the feedthrough pins 353(1)-353(4). As such, any fluid ingress path that bridges between any of the feedthrough pins 353(5)-353(7) and any of the feedthrough pins 353(1)-353(4) will necessarily cross the electrical shielding member 364, namely the conductive layer 366 (i.e., the conductive layer 366 is it in intimate contact with surface of feedthrough surface where conductive fluid can accumulate, thus the conductive layer 366 is disposed in the fluid ingress path). Since, as noted, the conductive layer 366 is electrically connected to the ground pin 353(4) (and thus the ground element), any signals passing through the fluid ingress will be shorted to the ground element via the low impedance connection. Stated differently, the conductive layer 366 will short any signals passing thereto to the ground element of the hearing prosthesis, thereby shielding the input feedthrough pins 353(1) and 353(2) from interference (i.e., the electrical shielding member 364 makes the implantable sound sensors less susceptible to noise due to fluid ingress into the encapsulation at the feedthrough 350).

FIGS. 4A, 4B, and 4C are diagrams illustrating a portion of a feedthrough 450 in accordance with certain embodiments presented herein. More specifically, FIG. 4A is a perspective view of the portion of the feedthrough 450, FIG. 4B is a sectional view of the feedthrough 450, and FIG. 4C is an exploded view of the feedthrough 450. For ease of illustration, the feedthrough 450 is shown in FIGS. 4A, 4B, and 4C without the presence of any encapsulation. Although FIGS. 4A-4C illustrate an elliptically-shaped feedthrough, it is to be appreciated that embodiments presented herein may be implemented with feedthroughs having different shapes. For ease of description, FIGS. 4A-4C will be described together.

The feedthrough 450 comprises an insulator 454 that extends through an opening in a housing 429 of a hearing prosthesis (e.g., cochlear implant). The housing 429 may be formed from, for example, titanium, platinum, or another biocompatible material. The feedthrough 450 also comprises a plurality of feedthrough pins 453 that extend through insulator 454 from an outer (non-hermetic) surface 455 of the insulator 454 (sometimes referred to herein as the outer surface 455 of feedthrough 450) to an inner surface 457 of the insulator 454. In the embodiments of FIGS. 4A-4C, the feedthrough 450 includes seven (7) feedthrough pins, referred to as feedthrough pins 453(1), 453(2), 453(3), 453(4), 453(5), 453(6), and 453(7). It is to be appreciated that the inclusion of seven feedthrough pins is merely illustrative and that feedthroughs in accordance with certain embodiments presented herein may include different numbers of feedthrough pins.

In order to ensure that the housing 429 provides a hermetic seal between electrical components inside the housing 429 and the recipient's tissue and bodily fluid, the insulator 454 is hermetically attached/joined to the housing. As described elsewhere herein, depending on the techniques used to form the insulator 454 and/or the feedthrough pins 453, the insulator 454 may be attached to the housing 429 in a number of different manners. In certain embodiments, the insulator 454 is a monolithic element that is hermetically joined to the housing 429 through brazing, as described elsewhere herein. In other embodiments, the insulator 454 and the feedthrough pins 453 are formed through a layering process, also as described elsewhere herein. It is to be appreciated that the use of a monolithic insulator or the use of a multi-layer insulator are illustrative of the numerous techniques that may be used in accordance with certain embodiments presented herein to form the insulator 454 and/or join the insulator 454 to the housing 429.

As noted above, the feedthrough pins 453(1)-453(7) may be elongate wires (e.g., formed from platinum), interconnected traces, or other types of conductive pathways that pass electrical signals between electrical components located within the housing 429 and electrical components located outside of the housing 429. In the specific embodiments of FIGS. 4A-4C, feedthrough pins 453(1) and 453(2) are referred to as "input feedthrough" pins because they carry electrical signals (current) received at one or more implantable sound sensors (e.g., microphones, accelerometers, etc.) to components within the housing 429. Again, for ease of illustration, the one or more implantable sound sensors have been omitted from FIGS. 4A-4C. However, shown in FIGS. 4A-4C are portions of lead conductors 457(1) and 457(2) that may be used to electrically connect the one or more sound input elements to the feedthrough pins 453(1) and 453(2), respectively. The lead conductors 457(1) and 457(2) may be connected to the feedthrough pins 453(1) and 453(2), respectively, via gold brazing, conductive epoxy, solder, mechanical riveting, etc.

Feedthrough pin 453(3) is referred to as a "power pin" because it delivers operating power to the one or more implantable sound sensors, while the feedthrough pin 453(4) is referred to as a "ground pin." The ground pin 453(4) is electrically connected to a ground node/element of the hearing prosthesis via a low impedance electrical connection. The ground element is a component that serves as a zero voltage reference point within the hearing prosthesis, (i.e., a designated reference point against which other potentials in the circuit are measured, assigned a potential of zero volts). FIGS. 4A-4C also illustrate lead conductors 457(3) and 457(4) electrically connected (e.g., via gold brazing, conductive epoxy, etc.) to the feedthrough pins 453(3) and 453(4), respectively. These lead conductors 457(3) and 457(4) may be used to electrically connect the one or more sound input elements to the feedthrough pins 453(3) and 453(4), respectively.

In certain embodiments, the ground pin 453(4) may be a "common" ground pin that is connected to a "common ground element," while in other embodiments the ground pin 453(4) may be an "isolated" ground pin connected to an "isolated ground element." A common ground element is a ground element/node that is also used by the audio circuit of the hearing prosthesis. An isolated ground is a ground element that is electrically separated from the audio circuit. In certain examples, since the isolated ground is the ground for a part of the hearing prosthesis that is different from the audio circuit, the isolated ground may be less likely to cause interference with the audio circuit. In certain common ground embodiments, the ground pin 453(4) may be electrically connected to the system ground.

Returning to the embodiments of FIGS. 4A-4C, as noted the feedthrough 450 also includes feedthrough pins 453(5), 453(6), and 453(7). In these embodiments, the feedthrough pins 453(5), 453(6), and 453(7) are electrically connected to implanted electrodes of the hearing prosthesis and, as such, carry electrical signals between the implanted electrodes and electrical components within housing 429. Accordingly, the feedthrough pins 453(5), 453(6), and 453(7) are referred to herein as "electrode feedthrough pins." For ease of illustration the electrodes, as well as the lead conductors for connection to the electrodes, have been omitted from FIGS. 4A-4C.

As shown in FIGS. 4A-4C, the feedthrough 450 has a compact design in which the input feedthrough pins 453(1) and 453(2) are located in relatively close proximity to the electrode feedthrough pins 453(5), 453(6), and 453(7). As noted, in conventional arrangements, fluid ingress into the encapsulation could lead to the formation of conductive fluid ingress/leakage paths between one or more of the electrode feedthrough pins and one or more of the input feedthrough pins. Also as noted above, the formation of a conductive fluid ingress path leads to the potential for interference one or more of the feedthrough pins. The embodiments of FIGS. 4A-4C remediate the effects of conductive fluid paths through the formation of an electrical shielding member (electrical ground shield) 464 at the outer surface 455 of the insulator 454. The electrical shielding member 464 is positioned at the outer surface 455 so as to provide a grounding barrier between the input feedthrough pins 453(1) and 453(2) (e.g., feedthrough pins 453 that carry interference-susceptible signals) and electrode feedthrough pins 453(5), 453(6), and 453(7) (e.g., feedthrough pins that carry interference-inducing signals).

In the embodiments of FIGS. 4A-4C, the electrical shielding member 464 comprises a second insulator 467 with selectively metallized surfaces 466. The second insulator 467 may be formed from ceramic or another non-conductive element that is adhered (e.g., via conductive epoxy, conductive silicone, etc.) to the outer surface 455 of the insulator 454. The second insulator 467 may be, for example, a monolithic element, a multi-layer element, etc.

As noted, one or more surfaces 466 of the second insulator 467 are metallized with a conductive material (e.g., a metallization applied via ion sputtering and masking, ion sputtering and post-machining, electroplating/electrodeposition, etc.). In the example of FIGS. 4A-4C, the metallized surfaces include a first surface 466(1) and a second surface 466(2). The first metallized surface 466(1) is a surface of the second insulator 467 that extends away from the outer surface 455 of the insulator 454. As shown in FIG. 4A-4C, the first metallized surface 466(1) surrounds the outer edge of the second insulator 467. The second surface 466(2) is a surface of the second insulator 467 that is in proximity to the ground pin 453(4). The first and second metallized surfaces 466(1), 466(2) are electrically connected with one another.

As shown, the second insulator 467 surrounds the input feedthrough pins 453(1) and 453(2), as well as the power pin 453(3) and the ground pin 454(4). Since, as noted above, the first metallized surface 466(1) surrounds the outer edge of the second insulator 467, the first metallized surface 466(1) also surrounds the feedthrough pins 453(1)-453(4). That is, the first metallized surface 466(1) is physically located between the electrode pins 453(5)-453(7) and the feedthrough pins 453(1)-453(4). As such, any fluid ingress path that bridges between any of the feedthrough pins 453(5)-453(7) and any of the feedthrough pins 453(1)-453(4) will necessarily cross the electrical shielding member 464, namely the first metallized surface 466(1) (i.e., the first metallized surface 466(1) is it in intimate contact with surface 455 of feedthrough surface where conductive fluid can accumulate, thus the first metallized surface 466(1) is disposed in the fluid ingress path).

As noted above, the first and second metallized surfaces 466(1), 466(2) are electrically connected with one another and, as shown in FIGS. 4A-4C, the second metallized surface 466(2) is electrically connected to the ground pin 453(4) (and thus the ground element). As such, any signals passing through the fluid ingress will contact the first metallized surface 466(1) and be shorted to the ground element via the low impedance connection (e.g., via second metallized surface 466(2) and the ground pin 453(4)). Stated differently, the first and second metallized surfaces 466(1), 466(2) will short any signals passing thereto to the ground element of the hearing prosthesis, thereby shielding the input feedthrough pins 453(1) and 453(2) from interference (i.e., the electrical shielding member 464 makes the implantable sound sensors less susceptible to noise due to fluid ingress into the encapsulation at the feedthrough 450).

FIGS. 4A-4C illustrate an embodiment in which the electrical shielding member 464 includes a second insulator 467 with first and second metallized surface 466(1) and 466(2). It is to be appreciated that two metallized surfaces is illustrative and that other embodiments may include other numbers of metallized surfaces. In general, the metallized surfaces are arrangements so as to form a conductive element that fully surrounds the input feedthrough pins (or other feedthrough pins) and to form a low impedance connected to a ground pin and, accordingly, a ground element of the hearing prosthesis. The conductive element that fully surrounds the input feedthrough pins and the connection to the ground element form a grounding barrier that isolates the input feedthrough pins from the electrode feedthrough pins.

Figure 6:
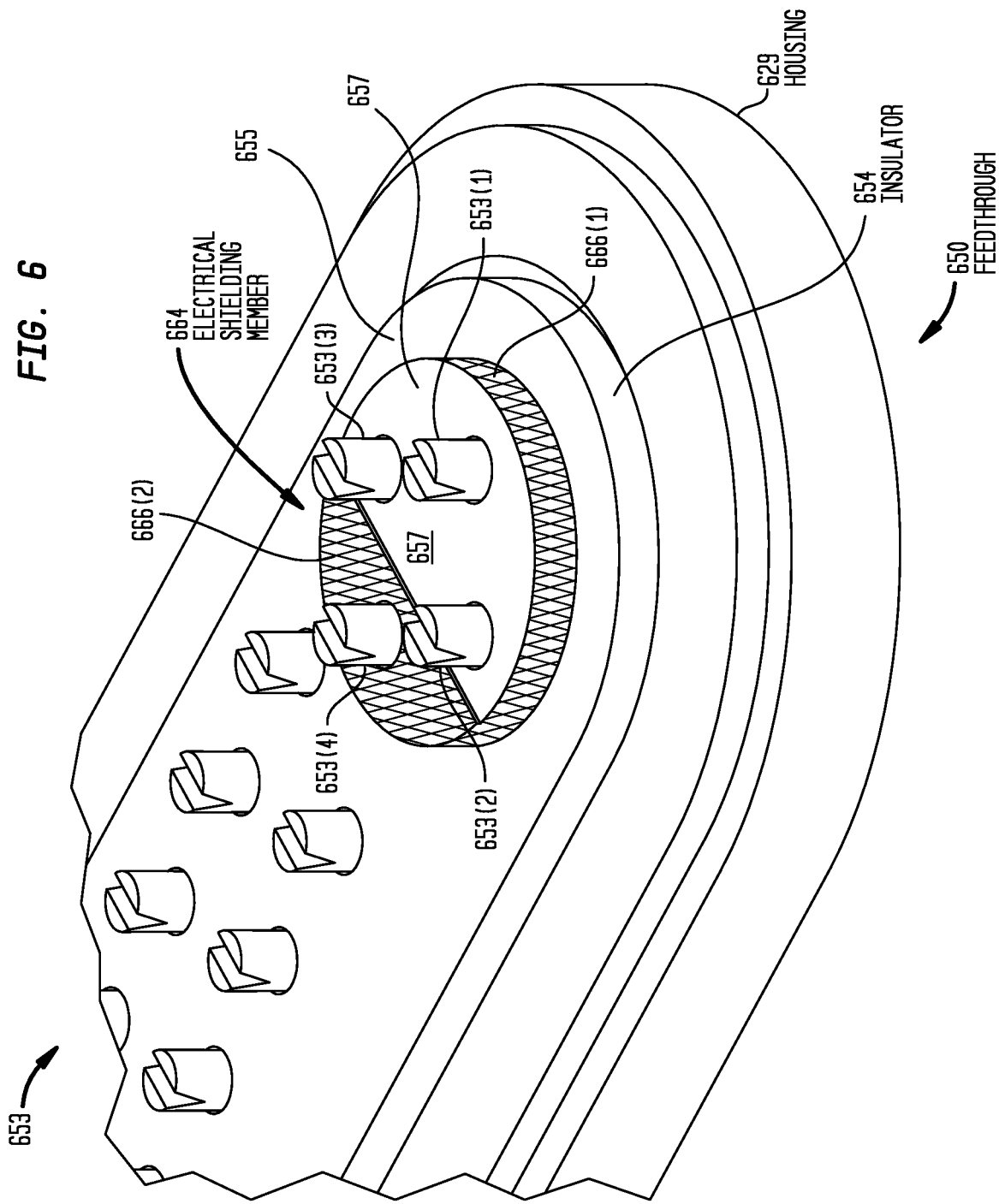
FIG. 6 is a perspective view of a portion of feedthrough and electrical shielding member, in accordance with certain embodiments presented herein.

It is to be appreciated that the specific shape for the second insulator shown in FIGS. 4A-4C is illustrative and that the insulators of electrical shielding members in accordance with certain embodiments presented herein may have other shapes. FIGS. 5 and 6 are two schematic diagrams illustrating electrical shielding members having different shaped insulators.

Referring first to FIG. 5, shown is an electrical shielding member 564 of a feedthrough 550. The feedthrough 550 comprises an insulator 554 that is hermetically attached to a housing 529. The feedthrough 550 also includes a plurality of feedthrough pins 553 which include, among other pins, input feedthrough pins 553(1) and 553(2), a power pin 553(3), and a ground pin 553(4). As noted, lead conductors (not shown in FIG. 5) may be electrically connected to the feedthrough pins 553(1)-553(4).

Similar to the embodiments of FIGS. 4A-4C, the electrical shielding member 564 includes a second insulator 567 that is attached to an outer surface 555 of the insulator 554. The second insulator 567 includes a first metallized surface 566(1) and a second metallized surface 566(2) that are electrically connected to one another (i.e., at least two surfaces of the insulator 567 are metallized with a conductive material). In the embodiment of FIG. 5, the first metallized surface 566(1) is a surface of the second insulator 567 that extends away from the outer surface 555 of the insulator 554. As shown in FIG. 5, the first metallized surface 566(1) surrounds the outer edge of the second insulator 567. The second surface 566(2) is a surface of the second insulator 567 that is in proximity to the ground pin 553(4).

As shown, the second insulator 567 surrounds the input feedthrough pins 553(1) and 553(2), as well as the power pin 553(3) and the ground pin 554(4). Since, as noted above, the first metallized surface 566(1) surrounds the outer edge of the second insulator 567, the first metallized surface 566(1) also surrounds the feedthrough pins 553(1)-553(4). That is, the first metallized surface 566(1) is physically located between the electrode pins (not shown in FIG. 5) and the feedthrough pins 553(1)-553(4). As such, any fluid ingress path that bridges between any of the feedthrough pins 553(1)-553(4) any other feedthrough pins will necessarily cross the electrical shielding member 564, namely the first metallized surface 566(1) (i.e., the first metallized surface 566(1) is it in intimate contact with surface 555 of feedthrough surface where conductive fluid can accumulate, thus the first metallized surface 566(1) is disposed in the fluid ingress path).

As noted above, the first and second metallized surfaces 566(1), 566(2) are electrically connected with one another and the second metallized surface 566(2) is electrically connected to the ground pin 553(4) (and thus the ground element). As such, any signals passing through the fluid ingress will contact the first metallized surface 566(1) and be shorted to the ground element via the low impedance connection (e.g., via second metallized surface 566(2) and the ground pin 553(4)). Stated differently, the first and second metallized surfaces 566(1), 566(2) will short any signals passing thereto to the ground element of the hearing prosthesis, thereby shielding the input feedthrough pins 553(1) and 553(2) from interference (i.e., the electrical shielding member 564 makes the implantable sound sensors less susceptible to noise due to fluid ingress into the encapsulation at the feedthrough 550).

Referring next to FIG. 6, shown is an electrical shielding member 664 of a feedthrough 650. The feedthrough 650 comprises an insulator 654 that is hermetically attached to a housing 629. The feedthrough 650 also includes a plurality of feedthrough pins 653 which include, among other pins, input feedthrough pins 653(1) and 653(2), a power pin 653(3), and a ground pin 653(4). As noted, lead conductors (not shown in FIG. 6) may be electrically connected to the feedthrough pins 653(1)-653(4).

Similar to the embodiments of FIGS. 4A-4C, the electrical shielding member 664 includes a second insulator 667 that is attached to an outer surface 655 of the insulator 654. The second insulator 667 includes a first metallized surface 666(1) and a second metallized surface 666(2) that are electrically connected to one another (i.e., at least two surfaces of the insulator 667 are metallized with a conductive material). In the embodiment of FIG. 6, the first metallized surface 666(1) is a surface of the second insulator 667 that extends away from the outer surface 655 of the insulator 654. As shown in FIG. 6, the first metallized surface 666(1) surrounds the outer edge of the second insulator 667. The second surface 666(2) is a surface of the second insulator 667 that is in proximity to the ground pin 653(4).

As shown, the second insulator 667 surrounds the input feedthrough pins 653(1) and 653(2), as well as the power pin 653(3) and the ground pin 654(4). Since, as noted above, the first metallized surface 666(1) surrounds the outer edge of the second insulator 667, the first metallized surface 666(1) also surrounds the feedthrough pins 653(1)-653(4). That is, the first metallized surface 666(1) is physically located between the electrode pins (not shown in FIG. 6) and the feedthrough pins 653(1)-653(4). As such, any fluid ingress path that bridges between any of the feedthrough pins 653(1)-653(4) any other feedthrough pins will necessarily cross the electrical shielding member 664, namely the first metallized surface 666(1) (i.e., the first metallized surface 666(1) is it in intimate contact with surface 655 of feedthrough surface where conductive fluid can accumulate, thus the first metallized surface 666(1) is disposed in the fluid ingress path).

As noted above, the first and second metallized surfaces 666(1), 666(2) are electrically connected with one another and the second metallized surface 666(2) is electrically connected to the ground pin 653(4) (and thus the ground element). As such, any signals passing through the fluid ingress will contact the first metallized surface 666(1) and be shorted to the ground element via the low impedance connection (e.g., via second metallized surface 666(2) and the ground pin 653(4)). Stated differently, the first and second metallized surfaces 666(1), 666(2) will short any signals passing thereto to the ground element of the hearing prosthesis, thereby shielding the input feedthrough pins 653(1) and 653(2) from interference (i.e., the electrical shielding member 664 makes the implantable sound sensors less susceptible to noise due to fluid ingress into the encapsulation at the feedthrough 650).

Figure 7:
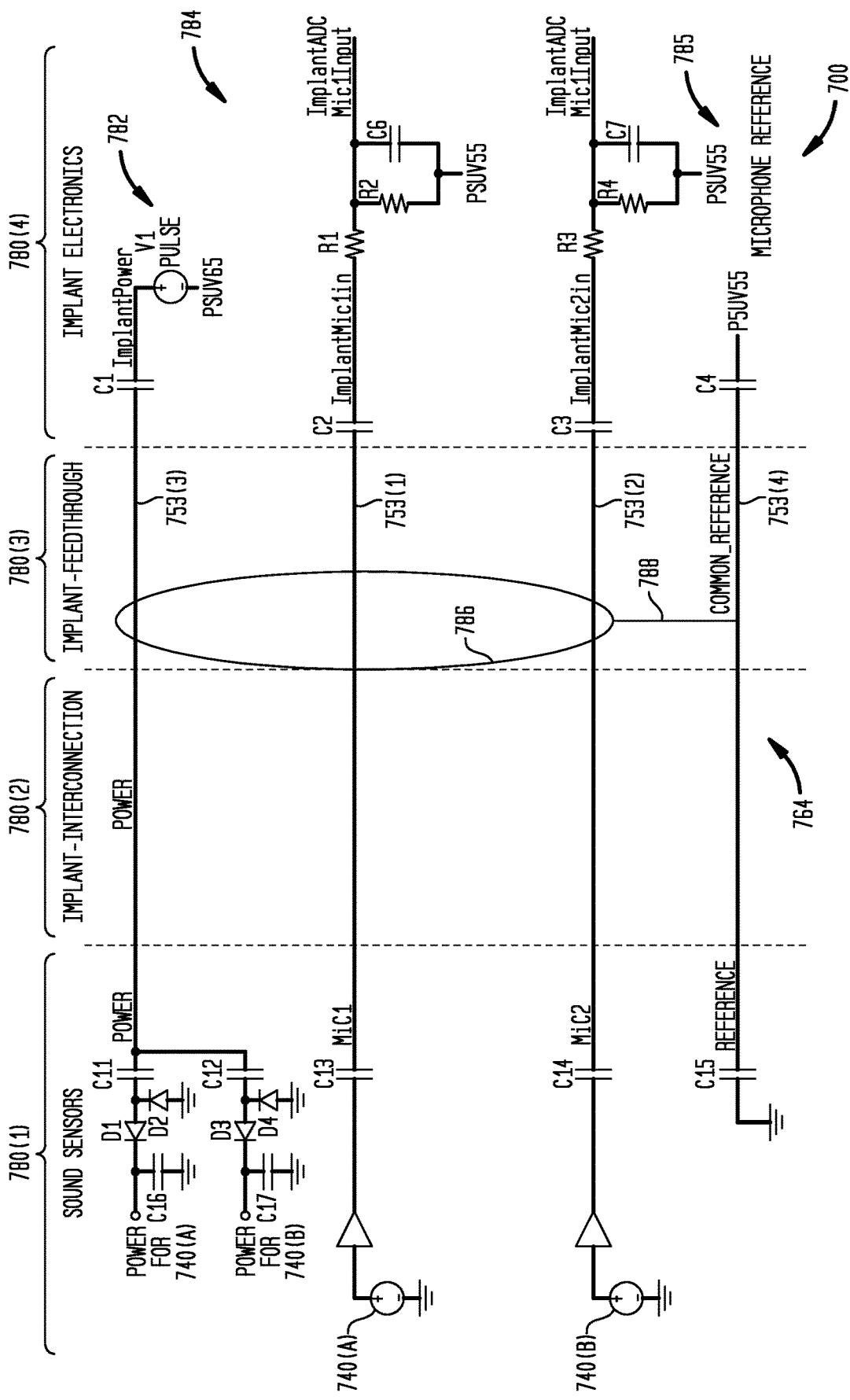
FIG. 7 is a schematic diagram illustrating electrical connection of an electrical shielding member to a ground element, in accordance with certain embodiments presented herein.
Figure 8:
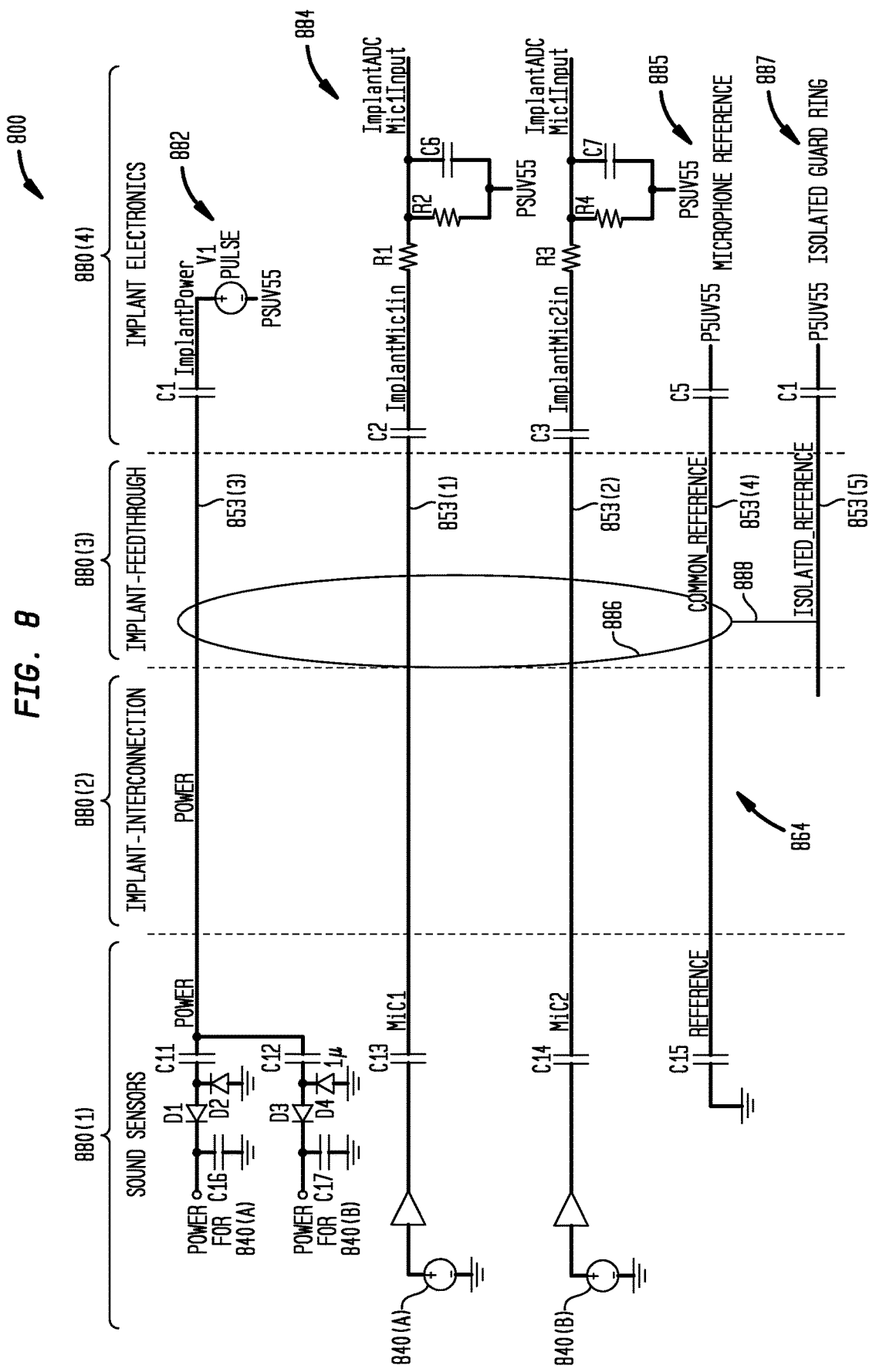
FIG. 8 is a schematic diagram illustrating electrical connection of an electrical shielding member to a ground element, in accordance with certain embodiments presented herein.

As noted above, electrical shielding members in accordance with certain embodiments presented herein provide a grounding barrier between feedthrough pins that carry signals that are susceptible to interference (interference-susceptible signals) and feedthrough pins that carry signals that are able to induce/cause interference (interference-inducing signals). The grounding barrier is formed by a conductive element that surrounds the feedthrough pins that carry the interference-susceptible signals and a low-impedance connection to a ground element via ground pin of the feedthrough. As noted above, in certain embodiments, the ground pin may be a "common" ground pin that is connected to a "common ground element," while in other embodiments the ground pin may be an "isolated" ground pin connected to an "isolated ground element." Also as noted above, a common ground element is a ground element/node that is also used by the audio circuit of the hearing prosthesis, while an isolated ground is a ground element that is electrically separated from the audio circuit. FIG. 7 is a schematic diagram illustrating an electrical shielding member connected to a common ground element (i.e., a common ground shielding member), while FIG. 8 is a schematic diagram illustrating an electrical shielding member connected to an isolated ground element (i.e., an isolated ground shielding member).

Referring first to FIG. 7, the schematic diagram includes four (4) sections 780(1), 780(2), 783(3), and 780(4) that each represent a different portion of an implantable hearing prosthesis 700. More specifically, section 780(1) represents a portion of the implantable hearing prosthesis 700 that is external to a hermetically sealed housing (not shown in FIG. 7). In the embodiment of FIG. 7, section 780(1) includes two implantable sound sensors 740(A) and 740(B).

Section 780(3) represents a hermetic feedthrough of the implantable hearing prosthesis 700. In this example, the hermetic feedthrough comprises at least four (4) feedthrough pins that include a first input feedthrough pin 753(1), a second input feedthrough pin 753(2), a power pin 753(3), and a common ground pin 753(4).

Section 780(2) represents electrical connections between the feedthrough pins 753(1)-753(4) and the implantable sound sensors 740(A) and 740(B). In this example, the first input feedthrough pin 753(1) is electrically connected to implantable sound sensor 740(A), while the second input feedthrough pin 753(2) is electrically connected to implantable sound sensor 740(B). The power pin 753(3) and the common ground pin 753(4) are each also connected to the implantable sound sensors 740(A) and 740(B). However, for ease of illustration, these connections have been omitted from FIG. 7.

Section 780(4) illustrates a portion of the electrical components of the implantable hearing prosthesis 700 that are located within the hermetically sealed housing. In particular, shown in FIG. 7 is a power source 782, an audio circuit 784, and a common ground element 785. The common ground element 785 is electrically connected to common ground pin 753(4).

FIG. 7 also schematically illustrates an electrical shielding member 764 in accordance with certain embodiments presented herein. The electrical shielding member 764 comprises a conductive element 786 that surrounds the feedthrough pins that carry the interference-susceptible signals (i.e., the first input feedthrough pin 753(1), the second input feedthrough pin 753(2)) and the power pin 753(3). The electrical shielding member 764 also comprises a low-impedance connection 788 to the ground element 785 via common ground pin 753(4).

As noted above, in the embodiment of FIG. 7, the common ground pin 753(4) is connected between the sound sensors 740(A) and 740(B) and the ground element 785. The ground element 785 is the ground or reference for the audio circuit 784. As such, the electrical shielding member 764 and the audio circuit 784 use a "common" (i.e., the same) ground or reference.

Referring next to FIG. 8, shown is a schematic diagram that includes four (4) sections 880(1), 880(2), 883(3), and 880(4) that each represent a different portion of an implantable hearing prosthesis 800. More specifically, section 880(1) represents a portion of the implantable hearing prosthesis 800 that is external to a hermetically sealed housing (not shown in FIG. 8). In the embodiment of FIG. 8, section 880(1) includes two implantable sound sensors 840(A) and 840(B).

Section 880(3) represents a hermetic feedthrough of the implantable hearing prosthesis 800. In this example, the hermetic feedthrough comprises at least five (5) feedthrough pins that include a first input feedthrough pin 853(1), a second input feedthrough pin 853(2), a power pin 853(3), a common ground pin 853(4), and an isolated ground pin 853(5).

Section 880(2) represents electrical connections between the feedthrough pins 853(1)-853(4) and the implantable sound sensors 840(A) and 840(B). In this example, the first input feedthrough pin 853(1) is electrically connected to implantable sound sensor 840(A), while the second input feedthrough pin 853(2) is electrically connected to implantable sound sensor 840(B). The power pin 853(3) and the common ground pin 853(4) are each also connected to the implantable sound sensors 840(A) and 840(B). However, for ease of illustration, these connections have been omitted from FIG. 8.

Section 880(4) illustrates a portion of the electrical components of the implantable hearing prosthesis 800 that are located within the hermetically sealed housing. In particular, shown in FIG. 8 is a power source 882, an audio circuit 884, a common ground element 885, and an isolated ground element 887. The common ground element 885 is electrically connected to common ground pin 853(4), while the isolated ground element 887 is electrically connected to isolated ground pin 853(5).

FIG. 8 also schematically illustrates an electrical shielding member 864 in accordance with certain embodiments presented herein. The electrical shielding member 864 comprises a conductive element 886 that surrounds the feedthrough pins that carry the interference-susceptible signals (i.e., the first input feedthrough pin 853(1), the second input feedthrough pin 853(2)), as well as the power pin 853(3) and the common ground pin 853(4). The electrical shielding member 864 also comprises a low-impedance connection 888 to the isolated ground element 887 via isolated ground pin 853(5).

As noted above, in the embodiment of FIG. 8, the common ground pin 853(4) is connected between the sound sensors 840(A) and 840(B) and the ground element 885. The ground element 885 is the ground or reference for the audio circuit 884. In addition, the isolated ground element 887 is electrically separated from the ground element 885 and, accordingly, from the sound sensors 840(A) and 840(B) and the audio circuit 884. Since the electrical shielding member 864 is connected to the isolated ground element 887, the electrical shielding member 864 and the audio circuit 884 use "isolated" (i.e., separate) grounds or references. In the embodiment of FIG. 8, since a separate ground reference is connected to the electrical shielding member 864, any current directed through the electrical shielding member 864 cannot affect the audio circuit.

FIG. 9 is a flowchart of a method 990 in accordance with embodiments presented herein. Method 990 begins at 991 where a housing, which that includes an aperture extending there through, is formed. At 992, an insulator is positioned in the aperture of the housing. The insulator comprises a plurality of feedthrough pins extending there through, where the plurality of feedthrough pins include a first feedthrough pin, a second feedthrough pin, and at least one ground feedthrough pin. At 993, the insulator is hermetically joined to the housing. At 994, an electrical shielding member is formed at an outer surface of the insulator between the first and second feedthrough pins. At 995, the housing, the housing, the insulator, the plurality of feedthrough pins, and the electrical shielding member are encapsulated in a biocompatible elastomer layer.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device, comprising:
    a hermetically-sealed biocompatible housing configured to be implanted in a recipient;
    an insulator extending through the housing, wherein the insulator comprises an outer surface that is external to the housing;
    a first feedthrough pin extending through the insulator and configured to carry first signals between a first functional component external to the housing and electronics within the housing;
    a second feedthrough pin extending through the insulator configured to carry second signals between a second functional component external to the housing and the electronics within the housing; and
    a conductive electrical shielding member positioned on the outer surface of the insulator between the first and second feedthrough pins, wherein the conductive electrical shielding member is configured to provide a grounding barrier between the first and second feedthrough pins to electrically shield the first feedthrough pin from the second signals and is insulated from the first and second feedthrough pins.

2. The implantable medical device of claim 1, further comprising:
    a biocompatible elastomer layer encapsulating the housing, the first feedthrough pin, the second feedthrough pin, and the conductive electrical shielding member.

3. The implantable medical device of claim 1, wherein the conductive electrical shielding member is disposed at the outer surface of the insulator surrounding at least the second feedthrough pin, and comprises a low impedance connection between the conductive electrical shielding member and a ground element of the implantable medical device.

4. The implantable medical device of claim 3, wherein the ground element is a common ground element that is electrically connected to the second functional component.

5. The implantable medical device of claim 3, wherein the ground element is an isolated ground element that is electrically separated from the second functional component.

6. The implantable medical device of claim 3, wherein the conductive electrical shielding member comprises:
    a recess formed in the outer surface of the insulator, wherein the conductive electrical shielding member is disposed in the recess and is electrically connected to a ground feedthrough pin extending through the insulator.

7. The implantable medical device of claim 3, wherein the conductive electrical shielding member is attached to the outer surface of the insulator and is electrically connected to a ground feedthrough pin extending through the insulator.

8. The implantable medical device of claim 3:
the conductive electrical shielding member is insulated from the first and second feedthrough pins by a second insulator attached to the outer surface of the insulator, wherein the conductive electrical shielding member comprises one or more outer surfaces of the second insulator that are metallized, wherein the one or more metallized outer surfaces of the second insulator are electrically connected to a ground feedthrough pin extending through the insulator.

9. The implantable medical device of claim 1, wherein the second functional component is an implantable sound sensor.

10. The implantable medical device of claim 1, wherein the first functional component is an electrode configured to deliver electrical stimulation to the recipient.

11. A method, comprising:
providing a housing that includes an aperture extending through the housing;
positioning an insulator in the aperture in the housing, wherein the insulator comprises a plurality of feedthrough pins extending through the insulator, and wherein the plurality of feedthrough pins include a first feedthrough pin, a second feedthrough pin, and at least one ground feedthrough pin;
hermetically joining the insulator to the housing;
forming a conductive electrical shielding member at an outer surface of the insulator that is external to the housing at a location between the first and second feedthrough pins and is configured to electrically shield the first feedthrough pin from signals associated with the second feedthrough pin;
insulating the conductive electrical shielding member from the first and second feedthrough pins; and
encapsulating the housing, the insulator, the plurality of feedthrough pins, and the conductive electrical shielding member in a biocompatible elastomer layer.

12. The method of claim 11, wherein forming the conductive electrical shielding member on the outer surface of the insulator includes:
electrically connecting the conductive electrical shielding member to the at least one ground feedthrough pin.

13. The method of claim 11, wherein forming the conductive electrical shielding member on the outer surface of the insulator comprises:
forming a recess in the outer surface of the insulator at least between the first feedthrough pin and the second feedthrough pin;
applying a metallization to the outer surface of the insulator so as that the metallization covers the recess and surrounds the second feedthrough pin;
removing portions of the metallization that are outside of the recess; and
electrically connecting the metallization to the at least one ground feedthrough pin.

14. The method of claim 11, wherein forming the conductive electrical shielding member on the outer surface of the insulator comprises:
attaching a metal foil to the outer surface of the insulator so as to at least surround the second feedthrough pin; and
electrically connecting the metal foil to the at least one ground feedthrough pin.

15. The method of claim 11, wherein insulating the conductive electrical shielding member from the first and second feedthrough pins comprises:
attaching a second insulator to the outer surface of the insulator at least between the first feedthrough pin and the second feedthrough pin, wherein the second insulator includes selected metallized surfaces that surround at least the second feedthrough pin; and
electrically connecting the selected metallized surfaces to the at least one ground feedthrough pin.

16. An implantable medical device, comprising:
a hermetically-sealed biocompatible housing that includes an aperture extending there through;
an insulator positioned in the aperture in the housing and having an outer surface that is external to the housing;
a plurality of feedthrough pins extending through the insulator, wherein the plurality of feedthrough pins include a first feedthrough pin, a second feedthrough pin, and at least one ground feedthrough pin;
a conductive element disposed at the outer surface of the insulator at a location between the second feedthrough pin and the first feedthrough pin, surrounding at least the second feedthrough pin, electrically connected to the at least one ground feedthrough pin and insulated from the first feedthrough pin and the second feedthrough pin, wherein the conductive element is configured to electrically shield the first feedthrough pin from signals associated with the second feedthrough pin; and
a biocompatible elastomer layer encapsulating the housing, the insulator, the plurality of feedthrough pins, and the conductive element.

17. The implantable medical device of claim 16, further comprising:
a recess formed in the outer surface of the insulator, wherein the conductive element is disposed in the recess.

18. The implantable medical device of claim 16, wherein the conductive element comprises a metal foil attached to the outer surface of the insulator.

19. The implantable medical device of claim 16, wherein the conductive element comprises:
selectively metallized surfaces of a second insulator attached to the outer surface of the insulator, wherein the second insulator insulates the conductive element from at least one of the first feedthrough pin and the second feedthrough pin.

20. The implantable medical device of claim 16, wherein first feedthrough pin is configured to carry first signals between a first functional component external to the housing and electronics within the housing, and wherein the second feedthrough pin extending through the insulator configured to carry second signals between a second functional component external to the housing and the electronics within the housing.

* * * * *